United States Patent [19]

Melvin, Jr.

[11] Patent Number: 4,686,224

[45] Date of Patent: Aug. 11, 1987

[54] OXINDOLE ANTIINFLAMMATORY AGENTS

[75] Inventor: Lawrence S. Melvin, Jr., Ledyard, Conn.

[73] Assignee: Pfizer Inc., New York, N.Y.

[21] Appl. No.: 762,998

[22] Filed: Aug. 6, 1985

Related U.S. Application Data

[63] Continuation-in-part of Ser. No. 666,953, Oct. 31, 1984, Pat. No. 4,644,005.

[51] Int. Cl.[4] .................. C07D 209/42; C07D 419/12; A61K 31/40
[52] U.S. Cl. .................................... 514/275; 514/339; 514/363; 514/371; 514/380; 514/414; 514/418; 544/331; 546/273; 548/139; 548/195; 548/246; 548/468; 548/486
[58] Field of Search ............... 548/486, 195, 246, 468, 548/139; 546/273; 544/331; 514/418, 414, 339, 371, 380, 363, 275

[56] References Cited

U.S. PATENT DOCUMENTS 3,749,731  7/1973  Zinnes ................................ 548/486

FOREIGN PATENT DOCUMENTS 155828  9/1985  European Pat. Off. ............ 548/486

*Primary Examiner*—Robert Gerstl
*Attorney, Agent, or Firm*—Charles J. Knuth; Albert E. Frost; James M. McManus

[57] ABSTRACT

Ketone containing 1-substituted oxindole-3-carboxamides as antiinflammatory agents prepared by reaction of the 1-substituted oxindole with an isocyanate or by aminolysis of the corresponding alkyl oxindole-3-carboxylate.

15 Claims, No Drawings

OXINDOLE ANTIINFLAMMATORY AGENTS

CROSS REFERENCE TO RELATED APPLICATIONS

This application is a continuation-in-part of copending application Ser. No. 666,953, filed Oct. 31, 1984 now U.S. Pat. No. 4,644,065.

BACKGROUND OF THE INVENTION

Rheumatoid arthritis, which affects 3-4% of the population, is characterized by inflammation and pain of joints. Although the etiology of rheumatoid arthritis is not known, both steroid and non-steroidal therapy have been employed to alleviate the symptoms of this illness. It is to this latter class of chemotherapeutic agents that the compounds of the present invention relate.

The potent non-steroidal antiinflammatory agent, Piroxicam, 4-hydroxy-2-methyl-N-(2-pyridyl)-2H-1,2-benzothiazine-3-carboxamide 1,1-dioxide was reported in U.S Pat. No. 3,591,584. More recently, antiinflammatory activity was found in simple non-steroidal oxindole-3-carboxamides, U.S. Pat. No. 3,634,453.

SUMMARY OF THE INVENTION

In accordance with the present invention, it has now been found that a group of novel oxindole carboxamide derivatives are useful as antiinflammatory agents.

The first group of compounds in this series are of the formula:

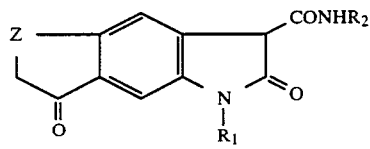

and a pharmaceutically acceptable salt thereof, wherein $R_1$ is phenyl or alkyl of one to three carbon atoms; Z is oxygen or methylene; and $R_2$ is phenyl, fluorophenyl, difluorophenyl; pyridyl, trifluoromethylphenyl, nitrophenyl, 2-thiazolyl or 5-methyl-2-thiazolyl.

Preferred in this series of compounds are those where $R_1$ is alkyl as defined and Z is methylene. Especially preferred are those compounds where $R_1$ is ethyl and $R_2$ is 4-fluorophenyl, 2,4-difluorophenyl or 3-trifluoromethylphenyl.

The second group of compounds of the present invention are of the formula:

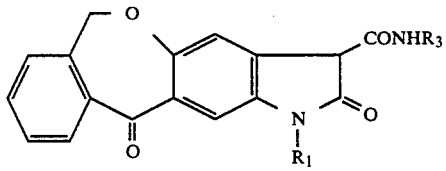

and a pharmaceutically acceptable salt thereof, wherein $R_1$ is phenyl or alkyl of one to three carbon atoms; and $R_3$ is phenyl, fluorophenyl, difluorophenyl, pyridyl, 2-thiazolyl or 5-methyl-2-thiazolyl.

Preferred within this group are compounds wherein $R_1$ is alkyl as defined. Especially preferred is the compound wherein $R_3$ is 2,4-difluorophenyl and $R_1$ is ethyl.

The third group of compounds of the present invention are of the formula

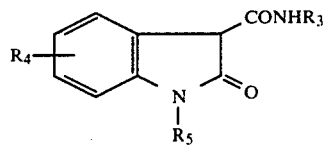

and a pharmaceutically acceptable salt thereof, wherein $R_3$ is phenyl, fluorophenyl, chlorophenyl, trifluoromethylphenyl, difluorophenyl, pyridyl, 2-thiazolyl, 5-methyl-2-thiazolyl, 5-methyl-3-isoxazolyl, 2-thiadiazolyl or 2-pyrimidyl; $R_4$ is a substituent at the 5, 6 or 7 position of the oxindole selected from alkanoyl of two to six carbon atoms, cycloalkanoyl of four to six carbon atoms, alkoxycarbonyl of two to three carbon atoms, 2-thenoyl, benzoyl, phenylacetyl or substituted benzoyl wherein substituent is fluoro, chloro, methyl or cyano; and $R_5$ is hydrogen or alkyl of one to three carbon atoms.

Preferred in this group of compounds are those wherein $R_5$ is alkyl as defined and $R_4$ is benzoyl Especially preferred are the compounds wherein $R_5$ is ethyl, $R_4$ is benzoyl at the 5-position of the oxindole and $R_3$ is 4-fluorophenyl or 5-methyl-2-thiazolyl. Also especially preferred is the compound wherein $R_5$ is methyl, $R_3$ is 4-fluorophenyl and $R_4$ is benzoyl at the 5-position of the oxindole.

A second preferred group of compounds are those wherein $R_5$ is hydrogen and $R_4$ is benzoyl. Especially preferred is the compound wherein $R_4$ is benzoyl at the 5-position of the oxindole and $R_3$ is 2,4-difluorophenyl.

A third preferred group of compounds are those wherein $R_5$ is alkyl as defined and $R_4$ is 2-thenoyl. Especially preferred are the compounds wherein $R_5$ is ethyl, $R_4$ is 2-thenoyl at the 5-position of the oxindole and $R_3$ is 4-fluorophenyl or 2,4-difluorophenyl.

A fourth preferred group of compounds are those wherein $R_5$ is alkyl as defined and $R_4$ is acetyl. Especially preferred is the compound wherein $R_5$ is ethyl, $R_4$ is acetyl at the 5-position of the oxindole and $R_3$ is 2,4-difluorophenyl.

Also part of the present invention is a method of treating an inflammatory disease in a mammalian subject, which comprises administering to said mammalian subject an inflammatory disease treating amount of a compound selected from one or more of the compounds of the present invention.

Also contemplated is a pharmaceutical composition, which comprises a pharmaceutically acceptable carrier and a compound of the present invention and wherein the weight-ratio of the -pharmaceutically acceptable carrier to said compound is in the ratio of from 1:4 to 20:1.

DETAILED DESCRIPTION

One of the processes employed in the preparation of the novel compounds of this invention consists of the interaction of an appropriate oxindole derivative with a requisite isocyanate as follows:

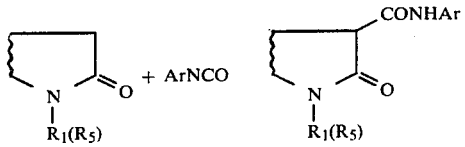

wherein $R_1$ and $R_5$ are as defined and Ar represents $R_2$ and $R_3$ as defined.

This reaction leading to the products of the instant invention is carried out in a reaction-inert solvent. Preferred solvents are polar, aprotic solvents such as dimethylformamide, diethylformamide, N-methyl-2-pyrrolidone or dimethylsulfoxide. Further it is preferred that the reaction be carried out in the presence of a base. Such bases include alkali and alkaline earth metal hydrides or a tertiary organic amine. The preferred base is sodium hydride.

In practice, the isocyanate is added to the oxindole derivative and base in the appropriate solvent. It is preferable to employ about a molar equivalent of the isocyanate and base, with best results achieved by using an excess of as much as 50% of each. It is preferred that the reagents be combined in the cold, generally from $-10°$ to $0°$ C., and that the reaction mixture be allowed to warm to room temperature. At from room temperature to $45°$ C. the reaction proceeds to completion in about a few minutes to overnight depending on the reactivity of the isocyanate.

Upon completion of the reaction, the product is isolated by adding the mixture to ice-water and treating with sufficient acid to provide a pH of between 2 and 5. The product can be filtered or extracted with a water immiscible solvent.

Purification can be by chromatography or by recrystallization from an appropriate solvent.

A second reaction leading to the novel products of the present invention consists of the interaction of an appropriate amine with an oxindole ester 4 as follows

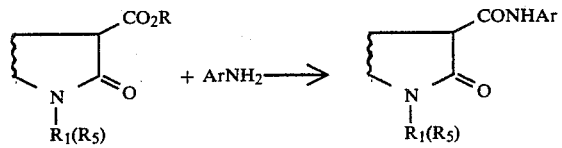

wherein $R_1$ and $R_5$ are as defined, R is alkyl of one to four carbon atoms and Ar is as defined.

This reaction leading to the products of the present invention is also carried out in a reaction-inert solvent. Preferred solvents are aprotic aromatic solvents such as benzene, toluene or xylene.

In practice, the reagents are combined in the appropriate solvent and heated to the reflux temperature of the solvent. It is preferable, in conducting this aminolysis reaction, to employ at least equimoles of ester and amine, although an excess of the amine, such as two equivalents, is especially preferred. To assist in removal of the alcohol by-product formed in the reaction a soxhlet containing molecular sieves is fitted to the reaction condenser. using reflux temperatures of the solvents the reaction is generally complete in 45–60 minutes.

The product can be isolated by cooling the reaction mixture and filtering the product or by adding the reaction mixture to an acidified aqueous solution followed by extraction of the product and removal of the solvent.

Purification can be carried out by recrystallization or chromatography.

The oxindole starting reagents for these processes are prepared by the herein described procedures. The requisite isocyanates are either commercially available or can be prepared by standard procedures known in the art, for instance, Zook and Wagner, Synthetic Organic Chemistry, John Wiley and Sons, Inc., New York, 1956, page 640.

In preparing the oxindole ester intermediate 4, wherein $R_4$ is alkanoyl at the 5- or 6-position, it is preferred that the carbonyl of the alkanoyl moiety be protected by ketal formation in order to minimize interaction of the dialkyl carbonate with the alkyl group of the alkanoyl moiety. The ketal group can be hydrolyzed after the oxindole ester has been reacted with the appropriate amine.

It is noted that a common characteristic of many non-steroidal antiinflammatory agents is their acidic nature. Each of the oxindole carboxamides of the instant invention shares this property and is an effective proton source.

Pharmaceutically acceptable salts of the compounds of the present invention are also therapeutic agents, wherein the preferred cations of said salts include the ammonium, sodium and potassium ions. The pharmaceutically acceptable salts of the compounds described herein are prepared by conventional procedures, as for example, by adding the acid to an aqueous solution containing an equivalent amount of the pharmaceutically acceptable base, i.e., a base containing one of the above preferred cations, followed by concentration of the resultant mixture to obtain the desired product. The bases can be selected from hydroxides, oxides or carbonates.

Also considered part of the present invention are prodrugs of the herein described compounds. These prodrugs, which have fewer gastrointestinal side effects, breakdown in situ to the parent compound.

As previously indicated, the oxindole carboxamides of the present invention and their pharmaceutically acceptable salts are useful antiinflammatory agents. These compounds are of value in alleviating swelling and inflammation which are symptomatic of rheumatoid arthritis and related disorders which are responsive to treatment with antiinflammatory agents. Either as individual therapeutic agents or as mixtures of therapeutic agents, they may be administered alone, but are generally administered with a pharmaceutical carrier selected on the basis of the chosen route of administration and standard pharmaceutical practice. For example, they may be administered orally in the form of tablets or capsules containing such excipients as starch, milk sugar or certain types of clay, etc. They may be administered orally in the form of elixirs or oral suspensions with the active ingredients combined with emulsifying and/or suspending agents. They may be injected parenterally, and for this use they, or appropriate derivatives, may be prepared in the form of sterile aqueous solutions. Such aqueous solutions should be suitably buffered, if necessary, and should contain other solutes such as saline or glucose to render them isotonic. The weight-ratio of the pharmaceutically-acceptable carrier to compound can be from 1:4 to 20:1.

The dosage required to reduce inflammation or swelling in arthritic subjects would be determined by the nature and extent of the symptoms. Generally, small doses will be required initially, with a gradual increase in the dose until the optimum level is determined. It will generally be found that when the composition is administered orally, larger amounts of the active ingredient will be required to produce the same level as produced by a smaller quantity administered parenterally. In general, from about 10 to about 300 mg. of active ingredient per kilogram of body weight, administered orally in single or multiple dose units, will effectively reduce inflammation and swelling. Parenteral administration requires doses of from about 5 to about 200 mg of active ingredient to achieve the same end point.

A standard procedure for detecting and comparing antiinflammatory activity of compounds is the carrageenin rat foot edema test, which is described by C. A. Winter et al., Proc. Soc. Exp. Biol., vol III, page 544 (1962).

In addition to being useful as antiinflammatory agents, the compounds of the present invention can be used in the treatment of asthma, bronchitis and psoriasis; they can also be used as analgesic agents.

The following examples are provided solely for the purpose of further illustration. Nuclear magnetic resonance spectra (NMR) were measured at 60 MHz for solutions in deuterochloroform ($CDCl_3$), perdeutero dimethyl sulfoxide (DMSO-$d_6$) or deuterium oxide ($D_2O$) or are noted otherwise, and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet; b, broad.

EXAMPLE 1

N-(2,4-Difluorophenyl)-1-ethyl-2,7-dioxo-2,3,5,6-tetrahydro-7H-cyclopenta[f]indole-3-carboxamide (1, $R_1=C_2H_5$, $R_2=2,4$-difluorophenyl, $Z=CH_2$)

To 103.5 mg. (4.5 mmoles) of sodium hydride in 4.5 ml. of dimethylformamide was added 645 mg. (3 mmoles) of 1-ethyl-2,7-dioxo-2,3,5,6-tetrahydro-7H-cyclopenta[f]indole followed after 20 minutes by 698 mg. (4.5 mmoles) of 2,4-difluoroisocyanate. After stirring for 30 minutes the reaction mixture was poured into a mixture of 2N hydrochloric acid and methylene chloride. The organic phase was separated, dried over sodium sulfate and concentrated to dryness. The residue was recrystallized from diisopropyl ether-methylene chloride, 872 mg. (79% yield), m.p. 190°–97° C. (dec.).

Anal. Calcd. for $C_{20}H_{16}O_3N_2F_2$: C, 64.9; H, 4.4; N, 7.6. Found: C, 64.7; H, 4.3; N, 7.7.

EXAMPLE 2

Employing theprocedure of Example 1, and starting with the appropriate regents, the following compounds were prepared:

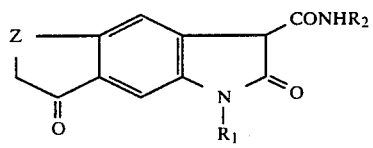

| $R_1$ | $R_2$ | Z | m.p. °C. | NMR($CDCl_3$)ppm. |
|---|---|---|---|---|
| $C_2H_5$ | phenyl | $CH_2$ | 130–135 | 1.29 (t, J=7Hz, $CH_3$), 2.7 ($CH_2$), 3.15 ($CH_2$), 3.9 (q, J=7Hz, $NCH_2$), 4.4 (s, CH), 6.9–7.7 (ArH), 7.91 (ArH) and 9.6 (NH). |
| $C_2H_5$ | 3-$CF_3$-phenyl | $CH_2$ | 180–188 | 1.31 (t, J=7Hz, $CH_3$), 2.75 ($CH_2$), 3.15 ($CH_2$), 3.92 (q, J=7Hz, $NCH_2$), 4.43 (s, CH), 7.1–8.0 (ArH) and 9.83 (NH). |
| $C_2H_5$ | 4-F-phenyl | O | 178–180 | 1.31 (t, J=7Hz, $CH_3$), 3.82 (q, J=7Hz, $CH_2$), 4.4 (CH), 4.65 (s, $OCH_2$), 6.8–7.6 (ArH), 7.6 (ArH) and 9.63 (NH). |
| $C_2H_5$ | 4-F-phenyl | $CH_2$ | 185–190 | 1.32 (t, J=7Hz, $CH_3$), 2.75 ($CH_2$), 3.18 ($CH_2$), 3.92 (d, J=7Hz, $NCH_2$), 4.42 (s, CH), 6.98 (d, J=8Hz, ArH), 7.2 (ArH), 7.56 (d, J=8Hz, ArH), 7.91 (ArH) and 9.63 (NH). |
| $C_2H_5$ | 4-$NO_2$-phenyl | $CH_2$ | 168–175 | 1.31 (t, J=7Hz, $CH_3$), 2.75, ($CH_2$), 3.17 ($CH_2$), 3.9 (q, J=7Hz, $NCH_2$), 4.42 (s, CH), 7.2 (ArH), 7.72 (d, J=9Hz, ArH), 7.9 (ArH), 8.16 (d, J=9Hz, ArH) and 10.13 (NH). |

EXAMPLE 3

Starting with the appropriate reagents and employing the procedure of Example 1, the following compounds are prepared:

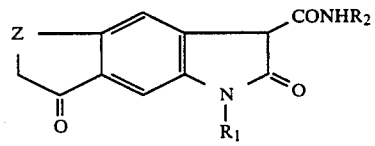

| $R_1$ | $R_2$ | Z |
|---|---|---|
| $CH_3$ | 2,4-difluorophenyl | $CH_2$ |
| $CH_3$ | 2-methyl-1,3-thiazol-4-yl | O |

-continued

| R₁ | R₂ | Z |
|---|---|---|
| CH₃ | 2-pyridyl | CH₂ |
| C₂H₅ | 2-thiazolyl | CH₂ |
| phenyl | phenyl | O |
| phenyl | 2,4-difluorophenyl | O |
| n-C₃H₇ | 2-pyridyl | CH₂ |
| n-C₃H₇ | 3,5-difluorophenyl | O |
| i-C₃H₇ | 4-nitrophenyl | O |
| i-C₃H₇ | 4-trifluoromethylphenyl | O |

EXAMPLE 4

N-(2,4-difluorophenyl)-1-ethyl-2,3,6,11-tetrahydro-2,11-dioxo-[2]benzoxepino[3,4-f]indole-3-carboxamide (2, R₁=C₂H₅, R₃=2,3-difluorophenyl)

To a slurry of 56 mg. (1.4 mmoles) of 60% sodium hydride in 3 ml. of dimethylformamide was added 293 mg. (1.0 mmole) of 1-ethyl-2,3,6,11-tetrahydro-2,11-dioxo-[2]benzoxepino[3,4-f]indole. After 15 minutes 217 mg. (1.4 mmoles) of 2,4-difluorophenylisocyanate in 0.75 ml. of dimethylformamide was added. After stirring for 30 minutes the reaction mixture was added to a mixture of ice water and methylene chloride. The organic phase was separated, dried over magnesium sulfate and concentrated to dryness to give the crude product, which was recrystallized from methylene chloride diisopropyl ether, 225 mg. (50% yield), m.p. 193°–199° C.

Anal. Calcd. for $C_{25}H_{18}F_2N_2O_4$: C, 67.0; H, 4.1; N, 6.3. Found: C, 66.9; H, 4.4; N, 6.2.

EXAMPLE 5

Starting with the appropriate isocyanate and 1-alkyl-2,3,6,11-tetrahydro-2,11-dioxo-[2]benzoxepino[3,4-f]indole and employing the procedure of Example 4, the following compounds are prepared:

| R₁ | R₃ |
|---|---|
| CH₃ | phenyl |
| CH₃ | 4-fluorophenyl |
| CH₃ | 3-fluorophenyl |
| CH₃ | 2,4-difluorophenyl |
| CH₃ | 2-pyridyl |
| C₂H₅ | phenyl |
| C₂H₅ | 4-methyl-2-thiazolyl |
| C₂H₅ | 2-fluorophenyl |
| C₂H₅ | 3,4-difluorophenyl |

-continued

[Structure: benzoyloxindole with CONHR3, methyl, and N-R1]

| R₁ | R₃ |
|---|---|
| n-C₃H₇ | 2,4-difluorophenyl |
| n-C₃H₇ | 4-fluorophenyl |
| i-C₃H₇ | 2,4-difluorophenyl |
| C₂H₅ | thiazol-2-yl |

EXAMPLE 6

N-(4-Fluorophenyl)-1-ethyl-5-benzoyloxindole-3-carboxamide (3, R₃=4-fluorophenyl, R₄=5-benzoyl, R₅=ethyl)

A mixture of 1.0 g. (2.96 mmoles) of ethyl 5-benzoyloxindole-3-carboxylate and 560 ul. (5.92 mmoles) of 4-fluoroaniline in 50 ml. of benzene were heated to reflux through a soxhlet filled with 4A molecular sieves for 45 minutes. The reaction mixture was cooled in ice and added to a mixture of 400 ml. of 2N hydrochloric acid and 200 ml. of methylene chloride. The organic phase was separated dried over magnesium sulfate and concentrated to give 1.26 g. of crude product, which was recrystallized from diisopropyl ether - methylene chloride, 611 mg. (51.3% yield), m.p. 125°–128° C.

Anal. Calcd. for C₂₄H₁₉O₃N₂F: C, 71.6; H, 4.8; N, 7.0. Found: C, 71.8; H, 5.0; N, 6.9.

EXAMPLE 7

Starting with the appropriate ethyl benzoyloxindole-3-carboxylate and amine, and employing the procedure of Example 6, the following compounds were prepared:

[Structure: X-substituted benzoyl indolinone with CONHR3 and N-R5]

| R₃ | Substitution Position | X | R₅ | m.p. °C |
|---|---|---|---|---|
| 4-methylthiazol-2-yl | 5- | H— | —C₂H₅ | 187 |
| 2,4-difluorophenyl | 5- | H— | —C₂H₅ | 147–149 |
| pyridyl | 5- | H— | —C₂H₅ | 242–245 |
| 2,4-difluorophenyl | 7- | H— | —H | 195–200 |
| 4-fluorophenyl | 7- | H— | —H | 213–217 |
| phenyl | 7- | H— | —H | 194–195 |
| 4-methylthiazol-2-yl | 7- | H— | —H | 258 (dec.) |

The NMR (d₆-DMSO) spectrum showed absorption at 1.2 (t, J=7Hz, CH₃), 2.3 (s, CH₃), 3.91 (q, J=7Hz, CH₂) and 7.0–8.2 (m, ArH) ppm.

Anal. Calcd. for C₂₄H₁₈O₃N₂F₂: C, 68.6; H, 4.3; N, 6.7.
Found: C, 68.6; H, 4.4; N, 6.7.

Anal. Calcd. for C₂₃H₁₉O₃N₃: C, 71.7; H, 5.0; N, 10.9.
Found: C, 71.7; H, 5.0; N, 10.9.

Anal. Calcd. for C₂₂H₁₄O₃N₂F₂: C, 67.4; H, 3.6; N, 7.1.
Found: C, 66.9; H, 3.9; N, 7.1.

Anal. Calcd. for C₂₂H₁₅O₃N₂F: C, 70.6; H, 4.0; N, 7.5.
Found: C, 70.3; H, 4.2; N, 7.4.

Anal. Calcd. for C₂₂H₁₆O₃N₂: C, 74.2; H, 4.5; N, 7.9.
Found: C, 74.0; H, 4.6; N, 7.7.

The NMR (D₆-DMSO) spectrum showed absorption at 2.3 (s, CH₃), 6.92 (bs, NH), 7.62 (bs, ArH) and 8.1 (m, ArH) ppm.

-continued

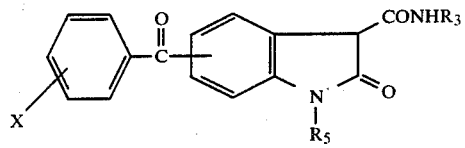

| R₃ | Substitution Position | X | R₅ | m.p. °C |
|---|---|---|---|---|
| 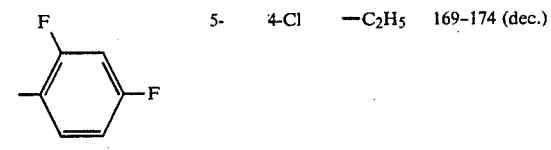 | 5- | 4-Cl | —C₂H₅ | 170–174 (dec.) |

Anal. Calcd. for $C_{24}H_{18}O_3N_2FCl$: C, 66.0; H, 4.2; N, 6.4.
Found: C, 66.5; H, 4.2; N, 6.3.

| | 5- | 4-Cl | —C₂H₅ | 169–174 (dec.) |
|---|---|---|---|---|
| 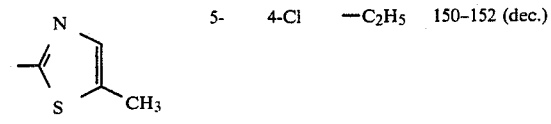 | | | | |

Anal. Calcd. for $C_{24}H_{17}O_3N_2F_2Cl$: C, 63.4; H, 3.8; N, 6.2.
Found: C, 63.9; H, 3.8; N, 6.0.

| | 5- | 4-Cl | —C₂H₅ | 150–152 (dec.) |
|---|---|---|---|---|
| 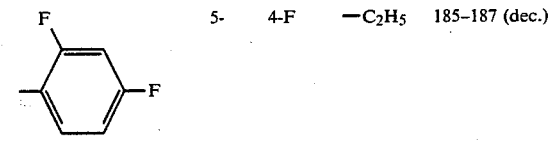 | | | | |

Anal. Calcd. for $C_{22}H_{18}O_3SN_3Cl$: C, 60.1; H, 4.1; N, 9.6.
Found: C, 59.4; H, 4.0; N, 9.4.

| | 5- | 4-F | —C₂H₅ | 185–187 (dec.) |
|---|---|---|---|---|
| 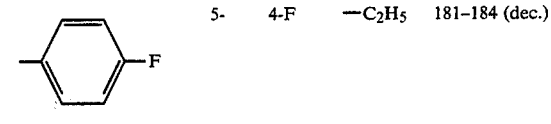 | | | | |

Anal. Calcd. for $C_{24}H_{17}O_3N_2F_3$: C, 65.8; H, 3.9; N, 6.4.
Found: C, 65.4; H, 3.8; N, 6.2.

| | 5- | 4-F | —C₂H₅ | 181–184 (dec.) |
|---|---|---|---|---|
| 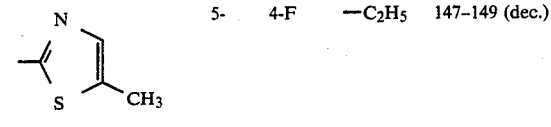 | | | | |

Anal. Calcd. for $C_{24}H_{18}O_3N_2F_2$: C, 68.6; H, 4.3; N, 6.7.
Found: C, 68.5; H, 4.4; N, 6.6.

| | 5- | 4-F | —C₂H₅ | 147–149 (dec.) |
|---|---|---|---|---|
| 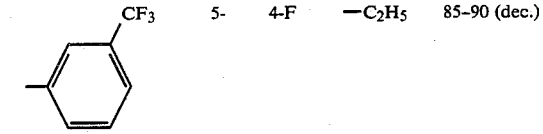 | | | | |

Anal. Calcd. for $C_{22}H_{18}O_3SN_3F$: C, 62.4; H, 4.3; N, 9.9.
Found: C, 62.8; H, 4.3; N, 9.6.

| CF₃ (on phenyl) | 5- | 4-F | —C₂H₅ | 85–90 (dec.) |
|---|---|---|---|---|

Anal. Calcd. for $C_{25}H_{18}O_3N_2F_4$: C, 63.8; H, 3.9; N, 6.0.
Found: C, 64.0; H, 3.9; N, 5.6.

-continued

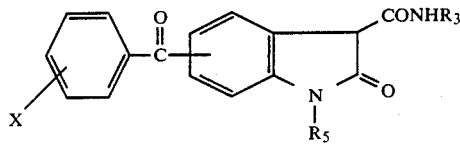

| R₃ | Substitution Position | X | R₅ | m.p. °C |
|---|---|---|---|---|
| 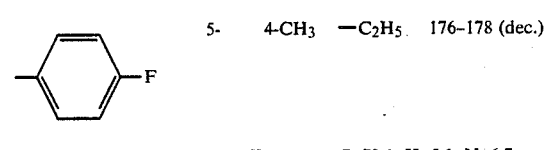 | 5- | 4-CH₃ | —C₂H₅ | 161–163 (dec.) |

Anal. Calcd. for $C_{25}H_{20}O_3N_2F_2$: C, 69.1; H, 4.6; N, 6.5.
Found: C, 68.9; H, 4.5; N, 6.4.

| 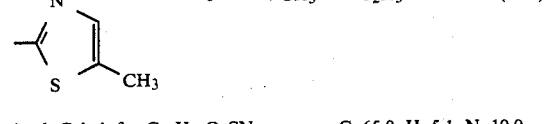 | 5- | 4-CH₃ | —C₂H₅ | 176–178 (dec.) |
|---|---|---|---|---|

Anal. Calcd. for $C_{25}H_{21}O_3N_2F$: C, 72.1; H, 5.1; N, 6.7.
Found: C, 71.7; H, 4.9; N, 6.6.

|  | 5- | 4-CH₃ | —C₂H₅ | 132–135 (dec.) |
|---|---|---|---|---|

Anal. Calcd. for $C_{23}H_{21}O_3SN_3$: C, 65.9; H, 5.1; N, 10.0.
Found: C, 65.2; H, 4.9; N, 9.4.

| CF₃ (on phenyl) | 5- | 4-CH₃ | —C₂H₅ | 136–139 (dec.) |
|---|---|---|---|---|

Anal. Calcd. for $C_{26}H_{21}O_3N_2F_3$: C, 67.0; H, 4.5; N, 6.0.
Found: C, 66.7; H, 4.4; N, 5.8.

EXAMPLE 8

N-(4-Fluorophenyl)-1-methyl-7-benzoyloxindole-3-carboxamide (3, R₃=4-fluorophenyl, R₄=7-benzoyl, R₅=CH₃)

To a slurry of 191 mg. of sodium hydride in 1.5 ml. of dimethylformamide cooled in an ice bath was added 1.0 g. (3.98 mmoles) of 1-methyl-7-benzoyloxindole in 2 ml. of the same solvent. After the evolution of hydrogen gas ceased (15 minutes) 644 ul. (5.97 mmoles) of 4-fluorophenylisocyanate was added, and the reaction mixture allowed to stir for 30 minutes. The reaction mixture was then poured into a mixture of 250 ml. of ice and 2N hydrochloric acid and 100 ml. of methylene chloride. The organic phase was separated, dried over magnesium sulfate and concentrated to give 2.0 g. of a residue, which was chromatographed on 80 g. of silica gel using methylene chloride as the eluent. The fractions containing the product were combined and concentrated to dryness. The residue was recrystallized from diisopropyl ether - methylene chloride, 631 mg. (41% yield), m.p. 173–177.

The NMR (CDCl₃) spectrum showed absorption at 3.09 (s, CH₃), 4.43 (s, CH), 6.8-8.0 (ArH) and 9.53 (s, NH) ppm.

Similarly were prepared N-(4-fluorophenyl)-1-ethyl-5-(4-cyanobenzoyl)oxindole-3-carboxamide, m.p. 168°-171° C., N-(2-fluorophenyl)-1-ethyl-5-(4-cyanobenzoyl)oxindole-3-carboxamide, m.p. 165°-167° C., N-(2,4-difluorophenyl)-1-ethyl-5-(4-cyanobenzoyl)oxindole-3-carboxamide, m.p. 196°-198° C. and N-(4-fluorophenyl)-1-ethyl-5-phenylacetyloxindole-3-carboxamide, m.p. 179°-180° C.

EXAMPLE 9

N-(2,4-Difluorophenyl)-1-ethyl-6-benzoyloxindole-3-carboxamide (3, $R_3$=2,4-difluorophenyl, $R_4$=6-benzoyl, $R_5$=$C_2H_5$)

To a slurry of 48 mg. (2 mmoles) of sodium hydride in 2 ml. of dimethylformamide was added 300 mg. (1.13 mmoles) of 1-ethyl-6-benzoyloxindole followed after 20 minutes by the addition of 310 mg. (2 mmoles) of 2,4-difluorophenylisocyanate. After stirring for 30 minutes the reaction was added to a mixture of 2N hydrochloric acid and methylene chloride. The organic phase was separated, dried over magnesium sulfate and concentrated to dryness. The residue was recrystallized from diisopropyl ether - methylene chloride to give 371 mg. (78% yield) of the desired product, m.p. 149°-151° C.

The NMR (CDCl₃) spectrum showed absorption at 1.31 (t, J=7 Hz, CH₃), 3.92 (q, J=7 Hz, CH₂), 4.45 (s, CH), 6.6-8.4 (m, ArH) and 9.85 (bs, NH) ppm.

EXAMPLE 10

Employing the procedure of Example 9, and starting with the appropriate 6-benzoyloxindole and isocyanate, the following compounds are prepared:

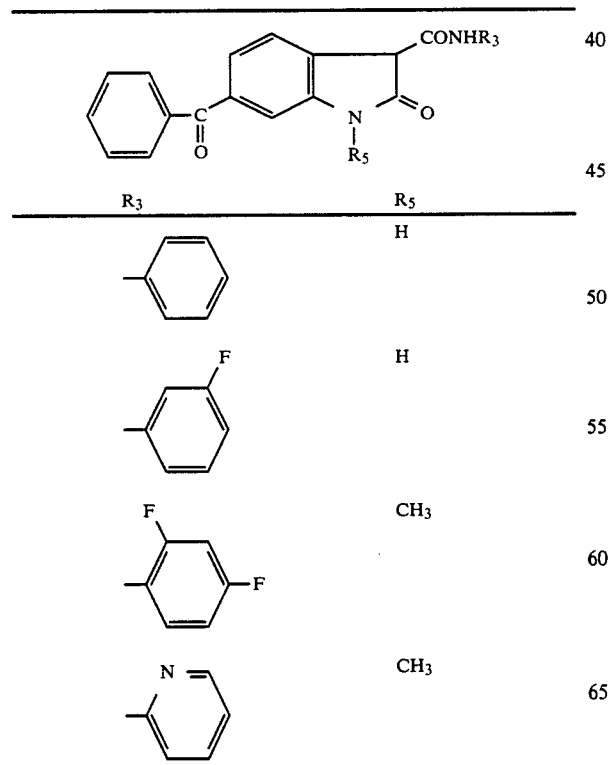

| $R_3$ | $R_5$ |
|---|---|
| phenyl | H |
| 2-fluorophenyl | H |
| 2,4-difluorophenyl | CH₃ |
| 2-pyridyl | CH₃ |
| 2-pyridyl | C₂H₅ |
| 2-methyl-5-thiazolyl | C₂H₅ |
| 2,5-difluorophenyl | C₂H₅ |
| 4-fluorophenyl | n-C₃H₇ |
| 2,3-difluorophenyl | n-C₃H₇ |
| phenyl | i-C₃H₇ |
| 2-pyridyl | i-C₃H₇ |
| 4-pyridyl | i-C₃H₇ |
| 2-fluorophenyl | i-C₃H₇ |
| 2-thiazolyl | CH₃ |

EXAMPLE 11

N-(2,4-Difluorophenyl)-1-ethyl-5-(2-thenoyl)oxindole-3-carboxamide (3, R$_3$=2,4-difluorophenyl, R$_4$=5-thenoyl, R$_5$=C$_2$H$_5$ A mixture of 1.0 g. (2.91 mmoles) of ethyl 1-ethyl-5-(2-thenoyl)oxindole-3-carboxylate and 750 mg. (5.82 mmoles) of 2,4-difluoroaniline in 50 ml. of benzene was heated to reflux through a soxhlet filled with 4A molecular sieves for 45 minutes. The reaction mixture was poured into 400 ml. of 2N hydrochloric acid and 200 ml. of methylene chloride. The organic phase was separated, dried over magnesium sulfate and concentrated to dryness in vacuo. Recrystallization of the residue from diisopropyl ether - methylene chloride gave 714 mg. (57.6% yield) of the desired product, m.p. 165°–168° C.

The NMR (CDCl$_3$) spectrum showed absorption at 1.32 (t, J=7 Hz, CH$_3$), 3.87 (q, J=7 Hz, CH$_2$), 4.5 (s, CH), 6.6–7.3 (m, ArH), 7.6–8.4 (ArH) and 9.68 (s, NH) ppm.

EXAMPLE 12

Starting with the appropriate amine and ethyl 1-ethyl-5-(2-thenoyl)oxindole-3-carboxylate and employing the procedure of Example 11, the following compounds were prepared:

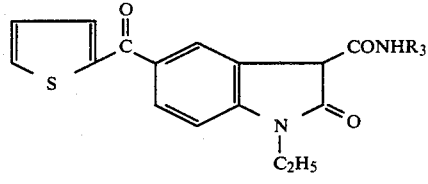

| R$_3$ | m.p., °C. | NMR, ppm. |
|---|---|---|
| 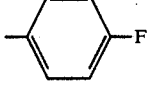 | 198 | a |
| 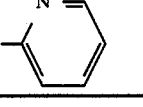 | 92–95 | b |
| 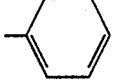 | 235 (dec.) | c |

$^a$(d$_6$-DMSO) 1.2 (t, J=7Hz, CH$_3$), 2.3 (s, CH$_3$), 3.89 (q, J=7Hz, CH$_2$) and 7.0–8.3 (m, ArH).
$^b$(CDCl$_3$) 1.31 (t, J=7Hz, CH$_3$), 3.84 (q, J=7Hz, CH$_2$), 4.41 (s, CH), 6.8–8.4 (m, ArH) and 9.5 (s, NH).
$^c$(D$_6$-DMSO + NaOD) 1.19 (t, J=7Hz), 3.93 (q, J=7Hz, CH$_2$) and 6.7–8.4 (ArH).

EXAMPLE 13

Using the procedure of Example 11 and starting with the requisite amine and alkyl 1-alkyl-5, 6 or 7-(2-thenoyl)oxindole-3-carboxylate, the following compounds are prepared:

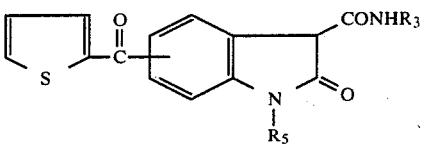

| R$_3$ | R$_5$ | Substitution Position |
|---|---|---|
| 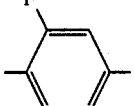 | H | 5- |
| 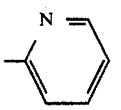 | H | 5- |
| 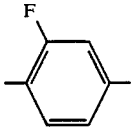 | CH$_3$ | 5- |
| 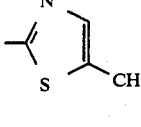 | C$_2$H$_5$ | 6- |
| 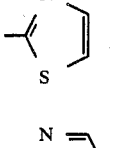 | CH$_3$ | 5- |
| 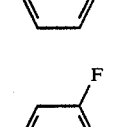 | C$_2$H$_5$ | 6- |
| 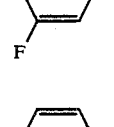 | H | 6- |
| 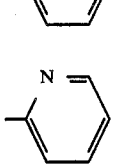 | C$_2$H$_5$ | 6- |
|  | C$_2$H$_5$ | 6- |
|  | CH$_3$ | 7- |

-continued

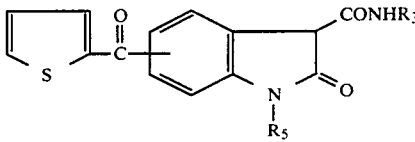

| R3 | R5 | Substitution Position |
|---|---|---|
| 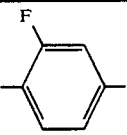 | C2H5 | 7- |
| 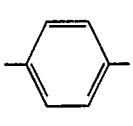 | H | 7- |
|  | n-C3H7 | 5- |
| 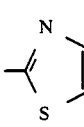 | n-C3H7 | 6- |
| 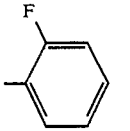 | n-C3H7 | 7- |
| 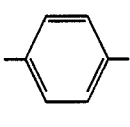 | n-C3H7 | 7- |
| 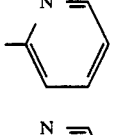 | i-C3H7 | 5- |
| 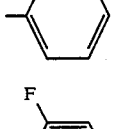 | i-C3H7 | 7- |
|  | i-C3H7 | 6- |

EXAMPLE 14

N-(2-Pyridyl)-7-acetyloxindole-3-carboxamide (3, R3=2-pyridyl, R4=7-acetyl, R5=H)

A mixture of 800 mg. (3.2 mmoles) of ethyl 7-acetyloxindole-3-carboxylate and 1.22 g. (12.7 mmoles) of 2-aminopyridine in 3.2 ml. of dimethylformamide was heated at 80° C. for 24 hours under a nitrogen atmosphere. The reaction mixture was added to 100 ml. of 2N hydrochloric acid and the solids filtered, washed with water and dried, 670 mg. The solids were triturated with methylene chloride, washed with water and dissolved in 50 ml. of water to which 1N sodium hydroxide solution was added until a solution resulted. The product was precipitated by the addition of 4N hydrochloric acid, and isolated by centrifugation, 219 mg. (23% yield), m.p. 240° C. (dec.).

The NMR (d6-DMSO+NaOD) spectrum showed absorption at 2.52 (s, CH3) and 6.6–8.4 (m, ArH) ppm.

EXAMPLE 15

N-(4-Fluorophenyl)-7-acetyloxindole-3-carboxamide (3, R3=4-fluorophenyl, R4=7-acetyl, R5=H)

A mixture of 1.0 g. (4.0 mmoles) of ethyl 7-acetyloxindole-3-carboxylate and 1.79 g (16.2 mmoles) of 4-fluoroaniline in 4 ml. of dimethylformamide was heated to 80° C. under a nitrogen atmosphere for one hour. The reaction mixture was poured into 600 ml. of cold 2N hydrochloric acid, and the resulting precipitate filtered and dried in vacuo, 1.1 g. The crude material was recrystallized from diisopropyl ether - methylene chloride, 297 mg. (23.5% yield), m.p. 226°–229° C.

The NMR (d6-DMSO) spectrum showed absorption at 2.6 (s, CH3), 7.0–8.0 (m, ArH) and 10.5 (bs) ppm.

EXAMPLE 16

Starting with the requisite ethyl 7-acetyloxindole-3-carboxylate and the appropriate amine, and employing the procedure of Example 15, the following compounds are prepared:

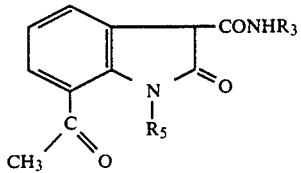

| R3 | R5 |
|---|---|
| 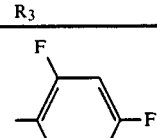 | H— |
| 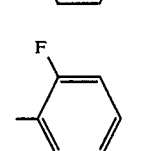 | H— |
| 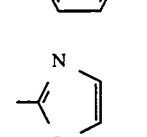 | H— |
| 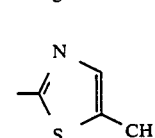 | H— |

-continued

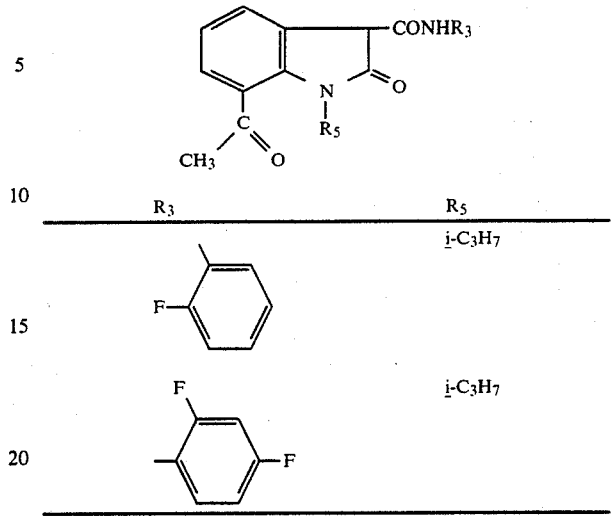

| $R_3$ | $R_5$ |
|---|---|
| (2,5-difluorophenyl) | H— |
| (4-fluorophenyl) | CH₃— |
| (2,4-difluorophenyl) | CH₃— |
| (2-pyridyl) | CH₃— |
| (2-thiazolyl) | C₂H₅— |
| (2,4-difluorophenyl) | C₂H₅ |
| (2-pyridyl) | C₂H₅ |
| (2-thiazolyl) | n-C₃H₇ |
| (5-methyl-2-thiazolyl) | n-C₃H₇ |
| (4-fluorophenyl) | i-C₃H₇ |

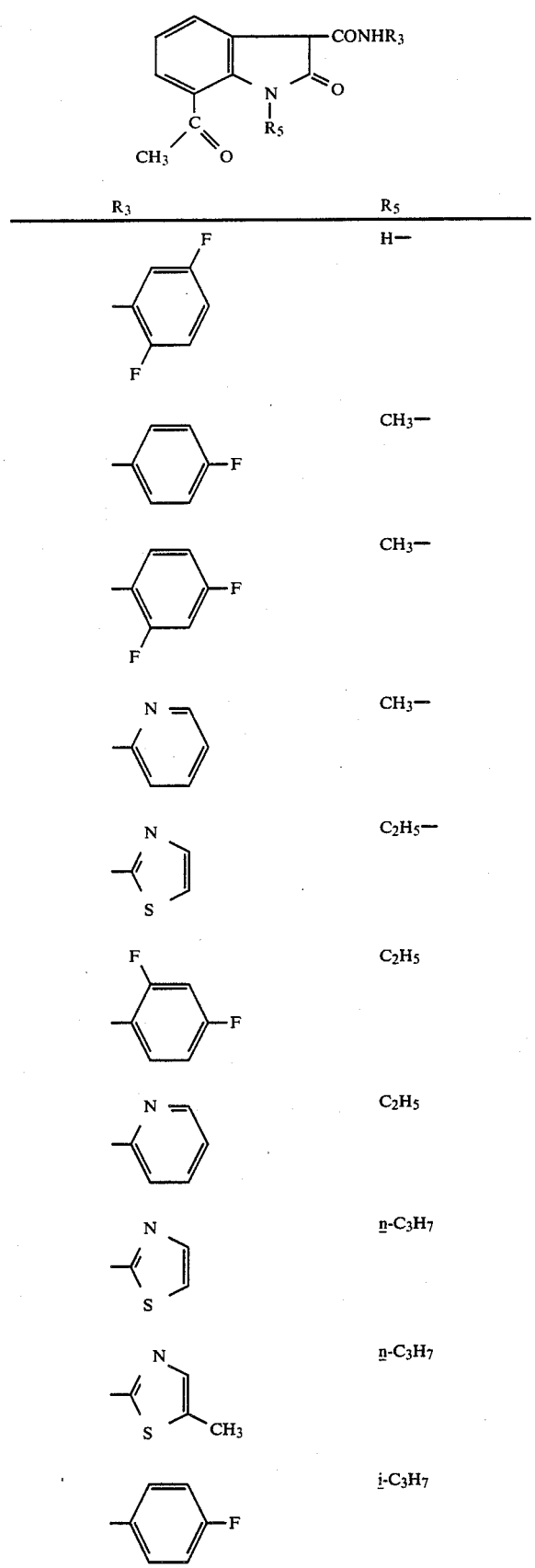

-continued

| $R_3$ | $R_5$ |
|---|---|
| (2-fluorophenyl) | i-C₃H₇ |
| (2,4-difluorophenyl) | i-C₃H₇ |

EXAMPLE 17

N-(2,4-Difluorophenyl)-1-ethyl-5-acetyloxindole-3-carboxamide (3, $R_3$=2,4-difluorophenyl, $R_4$=5-acetyl, $R_5$=C₂H₅)

A.
N-(2,4-difluorophenyl)-1-ethyl-5-(2-methyl-4,5-dihydro-1,3-dioxol-2-yl)oxindole-3-carboxamide A mixture of 1.0 g. (3.1 mmoles) of ethyl 1-ethyl-5-(2-methyl-4,5-dihydro-1,3-dioxol-2-yl)oxindole-3-carboxylate and 809 mg. (6.3 mmoles) of 2,4-difluoroaniline in 40 ml of benzene was heated to reflux through a soxhlet filled with 4A sieves for 45 minutes. The reaction mixture was cooled and poured into a mixture of 400 ml. 2N hydrochloric acid and 100 ml. of methylene chloride. The organic layer was separated, dried over magnesium sulfate and concentrated to give 1.24 g. of a solid residue. Recrystallization from diisopropyl ether - methylene chloride gave 1.0 g. of product (80% yield), m.p. 166°–170° C.

Anal. Calcd. for $C_{21}H_{20}O_4N_2F_2$: C, 62.7; H, 5.0; N, 7.0. Found: C, 62.6; H, 5.0; N, 7.0.

B.
N-(2,4-difluorophenyl)-1-ethyl-5-acetyloxindole-3-carboxamide

N-(2,4-Difluorophenyl)-1-ethyl-5-(2-methyl-4,5-dihydro-1,3-dioxol-2-yl)oxindol-3-carboxamide (636 mg., 1.58 mmoles) was dissolved in 15 ml. of tetrahydrofuran to which was added 10 ml. of 1N hydrochloric acid. The solution was stirred for one hour followed by the addition of an equal volume of water. The resulting precipitate was filtered, vacuum dried and recrystallized from diisopropyl ether - methylene chloride, 412 mg. (73% yield), m.p. 160°–161° C.

Anal. Calcd. for $C_{19}H_{16}O_3N_2F_2$: C, 63.7; H, 4.5; N, 7.8. Found: C, 63.5; H, 4.5; N, 7.7.

EXAMPLE 18

Starting with the appropriate amine and alkyl 1-ethyl-5-(2-alkyl-4,5-dihydro-1,3-dioxol-2-yl)oxindole-3-carboxylate and employing the procedure of Example 17 A-B, the following products were prepared:

Structure:

$Y-CO-$ on benzene ring fused to indolin-2-one with $R_5$ on N and $-CONH-R_3$ at 3-position.

| Y | $R_3$ | $R_5$ | m.p., °C |
|---|---|---|---|
| $CH_3$ | 4-methyl-2-thiazolyl (N=C(CH₃)-S-C(CH₃)=CH-) | $C_2H_5$ | 215(dec.) |

The NMR (d₆-DMSO + NaOD) spectrum showed absorption at 1.18 (5, J=7Hz, CH₃), 2.32 (s, CH₃), 2.56 (s, CH₃), 6.95 (m, ArH), 7.53 (dd, J=8 and 2Hz, ArH) and 8.40 (s, ArH) ppm.

| Y | $R_3$ | $R_5$ | m.p., °C |
|---|---|---|---|
| $CH_3$ | 3-CF₃-C₆H₄ | $C_2H_5$ | 100–105(dec.) |

Anal. Calcd. for $C_{20}H_{17}O_3N_2F_3$: C, 61.5; H, 4.4; N, 7.2.
Found: C, 61.4; H, 4.6; N, 7.0.

| Y | $R_3$ | $R_5$ | m.p., °C |
|---|---|---|---|
| $CH_3$ | 3-OCH₃-C₆H₄ | $C_2H_5$ | 140–141 |

Anal. Calcd. for $C_{20}H_{20}O_4N_2$: C, 68.2; H, 5.7; N, 8.0.
Found: C, 67.9; H, 5.9; N, 7.9.

| Y | $R_3$ | $R_5$ | m.p., °C |
|---|---|---|---|
| $CH_3$ | 2-F-C₆H₄ | $C_2H_5$ | 178–182(dec.) |

Anal. Calcd. for $C_{19}H_{17}O_3N_2F$: C, 67.1; H, 5.0; N, 8.2.
Found: C, 66.8; H, 5.1; N, 8.1.

| Y | $R_3$ | $R_5$ | m.p., °C |
|---|---|---|---|
| $CH_3$ | 2,3-difluoro-C₆H₃ | $C_2H_5$ | 215–218(dec.) |

Anal. Calcd. for $C_{19}H_{16}O_3N_2F_2$: C, 63.7; H, 4.5; N, 7.8.
Found: C, 63.5; H, 4.6; N, 7.7.

| Y | $R_3$ | $R_5$ | m.p., °C |
|---|---|---|---|
| $CH_3$ | 2,5-difluoro-C₆H₃ | $C_2H_5$ | 210–212(dec.) |

Anal. Calcd. for $C_{19}H_{16}O_3N_2F_2$: C, 63.7; H, 4.5; N, 7.8.
Found: C, 63.7; H, 4.7; N, 7.7.

| Y | $R_3$ | $R_5$ | m.p., °C |
|---|---|---|---|
| $CH_3$ | 4-Cl-C₆H₄ | $C_2H_5$ | 127–130(dec.) |

Anal. Calcd. for $C_{19}H_{17}O_3N_2Cl$: C, 64.0; H, 4.8; N, 7.9.
Found: C, 64.5; N, 5.6; N, 7.1.

| Y | $R_3$ | $R_5$ | m.p., °C |
|---|---|---|---|
| $CH_3$ | 4-F-C₆H₄ | $C_2H_5$ | 116–120(dec.) |

Anal. Calcd. for $C_{19}H_{17}O_3N_2F$: C, 67.1; H, 5.0; N, 8.2.
Found: C, 66.8; H, 5.2; N, 8.1.

| Y | $R_3$ | $R_5$ | m.p., °C |
|---|---|---|---|
| $CH_3$ | 2-Cl-C₆H₄ | $C_2H_5$ | 194–196(dec.) |

Anal. Calcd. for $C_{19}H_{17}O_3N_2Cl$: C, 64.0; H, 4.8; N, 7.9.
Found: C, 64.0; H, 4.8; N, 7.7.

| Y | $R_3$ | $R_5$ | m.p., °C |
|---|---|---|---|
| $CH_3$ | 3-F-C₆H₄ | $C_2H_5$ | 174–176.5(dec.) |

Anal. Calcd. for $C_{19}H_{17}O_3N_2F$: C, 67.1; H, 5.0; N, 8.2.
Found: C, 66.6; H, 5.0; N, 8.1.

| Y | $R_3$ | $R_5$ | m.p., °C |
|---|---|---|---|
| $CH_3$ | C₆H₅ | $C_2H_5$ | 190–192(dec.) |

Anal. Calcd. for $C_{19}H_{18}O_3N_2$: C, 70.8; H, 5.6; N, 8.7.
Found: C, 70.8; H, 5.6; N, 8.8.

| Y | $R_3$ | $R_5$ | m.p., °C |
|---|---|---|---|
| $CH_3(CH_2)_4$ | 2,4-difluoro-C₆H₃ | $C_2H_5$ | 119–120 |

Anal. Calcd. for $C_{23}H_{24}N_2O_3F_2$: C, 66.7; H, 5.8; N, 6.8.
Found: C, 66.7; H, 5.7; N, 6.6.

| Y | $R_3$ | $R_5$ | m.p., °C |
|---|---|---|---|
| $CH_3(CH_2)_4$ | 2-F-C₆H₄ | $C_2H_5$ | 127–128 |

Anal. Calcd. for $C_{23}H_{25}N_2O_3F\cdot\frac{1}{2}H_2O$: C, 68.1; H, 6.5; N, 6.9.
Found: C, 68.5; H, 6.3; N, 6.9.

| Y | $R_3$ | $R_5$ | m.p., °C |
|---|---|---|---|
| $CH_3(CH_2)_4$ | 4-methyl-2-thiazolyl | $C_2H_5$ | 190–191(dec.) | m/e Calcd. for $C_{21}H_{25}N_3O_3S$: 399.5
Found: 399.1

-continued

Structure: Y-C(=O)- attached to a 2-oxoindoline with CONH-R₃ at position 3 and R₅ on the nitrogen.

| Y | R₃ | R₅ | m.p., °C |
|---|----|----|----------|
| $CH_3(CH_2)_4$ | 3-(trifluoromethyl)phenyl | $C_2H_5$ | 129–131 |

Anal. Calcd. for $C_{24}H_{25}N_2O_3F_3$: C, 64.6; H, 5.6; N, 6.3.
Found: C, 64.4; H, 5.8; N, 6.2.

| $CH_3(CH_2)_4$ | 4-fluorophenyl | $C_2H_5$ | 174–175 |

Anal. Calcd. for $C_{23}H_{27}O_3N_2F$: C, 69.7; H, 6.4; N, 7.1.
Found: C, 68.9; H, 6.2; N, 6.9.

| $CH_3(CH_2)_4$ | 2,5-difluorophenyl | $C_2H_5$ | 119–120 |

Anal. Calcd. for $C_{23}H_{24}N_2O_3F_2$: C, 66.7; H, 5.8; 6.8.
Found: C, 66.7; H, 5.8; 6.7.

| $CH_3$ | 5-methylisoxazol-3-yl | $C_2H_5$ | 187–190 |

Anal. Calcd. for $C_{17}H_{17}N_3O_4$: C, 62.4; H, 5.2; N, 12.8.
Found: C, 61.6; H, 5.3; N, 12.4.

| $CH_3$ | 1,3,4-thiadiazol-2-yl | $C_2H_5$ | 230–231(dec.) |

Anal. Calcd. for $C_{15}H_{14}O_4O_3S$: C, 54.5; H, 4.3; N, 17.0.
Found: C, 54.3; H, 4.3; N, 16.8.

| $CH_3$ | pyrazinyl | $C_2H_5$ | 177–179(dec.) |

Anal. Calcd. for $C_{17}H_{16}N_4O_3$: C, 63.0; H, 5.0; N, 17.3.
Found: C, 62.3; H, 4.9; N, 17.1.

| $(CH_3)_2CH$ | 3-(trifluoromethyl)phenyl | $C_2H_5$ | 132–135 |

Anal. Calcd. for $C_{22}H_{21}N_2O_3F_3$: C, 63.2; H, 5.1; N, 6.7.
Found: C, 63.5; H, 5.2; N, 6.6.

| $(CH_3)_2CH$ | 2,4-difluorophenyl | $C_2H_5$ | 125.5–127.5 |

Anal. Calcd. for $C_{23}H_{29}O_4N_2F_2$: C, 65.3; H, 5.2; N, 7.3.
Found: C, 65.4; H, 5.3; N, 7.1.

| $(CH_3)_2CH$ | 2-fluorophenyl | $C_2H_5$ | 133–135 |

Anal. Calcd. for $C_{21}H_{21}N_2O_3F$: C, 68.5; H, 5.8; N, 7.6.
Found: C, 68.4; H, 5.7; N, 7.5.

| $\phi CH_2$ | 2,4-difluorophenyl | $C_2H_5$ | 118–120 |

Anal. Calcd. for $C_{25}H_{20}O_3N_2F_2$: C, 69.1; H, 4.6; N, 6.5.
Found: C, 69.2; H, 4.5; N, 5.8.

| $(CH_3)_3CCH_2$ | 2,4-difluorophenyl | $C_2H_5$ | — |

Anal. Calcd. for $C_{23}H_{27}N_2O_3F_2$: C, 66.2; H, 6.5; N, 6.7.
Found: C, 66.1; H, 5.7; N, 6.7.

| $(CH_3)_3CCH_2$ | 2,5-difluorophenyl | $C_2H_5$ | 133–135 |

Anal. Calcd. for $C_{23}H_{24}N_2O_3F_2$: C, 66.7; H, 5.8; N, 6.4.
Found: C, 66.5; H, 5.9; N, 6.6.

| $(CH_3)_3CCH_2$ | 3-(trifluoromethyl)phenyl | $C_2H_5$ | 120–122 |

Anal. Calcd. for $C_{24}H_{25}N_2O_3F_3$: C, 64.6; H, 5.7; N, 6.3.
Found: C, 64.3; H, 5.7; N, 6.1.

| $(CH_3)_3CCH_2$ | 4-fluorophenyl | $C_2H_5$ | 153–155 |

Anal. Calcd. for $C_{23}H_{25}N_2O_3F$: C, 69.7; H, 6.4; N, 7.0.
Found: C, 69.6; H, 6.2; N, 7.1.

-continued

[Structure: 5-Y-C(=O)-oxindole-3-CONH-R3, N-R5]

| Y | R3 | R5 | m.p., °C. |
|---|---|---|---|
| (CH3)3CCH2 | 2-F-phenyl | C2H5 | 135–137 |

Anal. Calcd. for C23H25N2O3F:   C, 69.2; H, 6.4; N, 7.2.
Found:                          C, 69.7; H, 6.3; N, 7.0.

EXAMPLE 19

Starting with the appropriate amine and the requisite ethyl 5 or 6-(2-methyl-4,5-dihydro-1,3-dioxol-2-yl)oxindole-3-carboxylate and using the procedure of Example 17, the following compounds are made:

[Structure: CH3C(=O)-oxindole-3-CONHR3, N-R5]

| R3 | R5 | Substitution Position |
|---|---|---|
| 2-pyridyl | H— | 5- |
| 2,4-difluorophenyl | H— | 5- |
| 4-fluorophenyl | H— | 5- |
| 2-thiazolyl | CH3— | 5- |
| 2,5-difluorophenyl | CH3 | 5- |
| 2-fluorophenyl | CH3 | 5- |

-continued

[Structure: CH3C(=O)-oxindole-3-CONHR3, N-R5]

| R3 | R5 | Substitution Position |
|---|---|---|
| 4-fluorophenyl | C2H5— | 5- |
| 2,4-difluorophenyl | C2H5 | 5- |
| 2-pyridyl | n-C3H7 | 5- |
| 4-methyl-2-thiazolyl | n-C3H7 | 5- |
| 4-fluorophenyl | i-C3H7 | 5- |
| phenyl | H | 6- |
| 4-fluorophenyl | H | 6- |
| 2,4-difluorophenyl | H | 6- |
| 2,4-difluorophenyl | CH3 | 6- |
| 4-pyridyl | CH3 | 6- |
| 2-thiazolyl | CH3 | 6- |

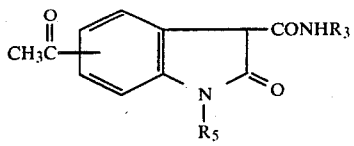

| R₃ | R₅ | Substitution Position |
|---|---|---|
| 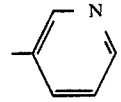 | C₂H₅ | 6- |
|  | C₂H₅ | 6- |
| 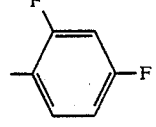 | n-C₃H₇ | 6- |
| 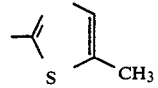 | n-C₃H₇ | 6- |

EXAMPLE 20

N-(2,4-Difluorophenyl)-1-ethyl-5-cyclopentylcarbonyloxindole-3-carboxamide(3, R₃=2,4-difluorophenyl, R₄=cyclopentylcarbonyl, R₅=C₂H₅

A mixture of 1.0 g. (3.04 mmoles) of ethyl 1-ethyl-5-cyclopentylcarbonyloxindole-3-carboxylate and 0.62 ml. (6.08 mmoles) of 2.4-difluoroaniline in 50 ml. of benzene was heated to reflux through a soxhlet filled with 4A sieves for 3 hours. The solution was concentrated to a dark oil which was taken up in methylene chloride and added to 1N hydrochloric acid. The organic layer was separated, washed with water and a brine solution and concentrated to an oil. The residue was dissolved in the minimum amount of methylene chloride and added with stirring to one equivalent of dimethylaminopyridine in 100 ml. of diethyl ether. The resulting precipitate was dissolved in methylene chloride and washed with 2N hydrochloric acid, water and a brine solution. The organic layer was separated, dried and concentrated to an oil. Treatment with hexane and diethyl ether gave 142 mg. of product, m.p. 148°–150° C.

Anal. Calcd. for C₂₃H₂₂N₂O₃F₂.H₂O: C, 64.2; H, 5.6; N, 6.5. Found: C, 64.4; H, 5.1; N, 6.4.

In a similar manner, N-(4-fluorophenyl)-1-ethyl-5-cyclopentylcarbonyloxindole-3-carboxamide, m.p. 170°–172° C.; N-(2,4-difluorophenyl)-1-ethyl-5-cyclopropylcarbonyloxindole-3-carboxamide, m.p. 179°–180° C.; N-(4-fluorophenyl)-1-ethyl-5-cyclopropyloxindole-3-carboxamide, m.p. 169°–170° C.; N-(2,4-difluorophenyl)-1-ethyl-5-ethoxycarbonyloxindole-3-carboxamide, m.p. 145°–150° C. (dec.); N-(2,4-difluorophenyl)-1-ethyl-5-methoxycarbonyloxindole-3-carboxamide, m.p. 147°–153° C.; and N-(4-fluorophenyl)-1-ethyl-5-methoxycarbonyloxindole-3-carboxamide, m.p. 159°–164° C. were prepared.

PREPARATION A

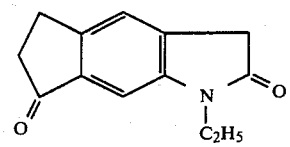

1-Ethyl-2,7-dioxo-2,3,5,6-tetrahydro-7H-cyclopenta[f]indole

A1. 1-ethyl-5-formyloxindole

To a solution of 32.2 g. (0.2 mole) of 1-ethyloxindole in 200 ml. of methylene chloride was added 44 ml. (0.4 mole) of titanium tetrachloride followed by 22.6 ml. (0.25 mole) of dichloromethyl methyl ether. The reaction was stirred for 10.5 days at 25° C. followed by the addition of additional titanium tetrachloride and dichloromethyl methyl ether every 48 hours. The reaction was poured onto 1 l. of ice and water and extracted with methylene chloride. Concentration of the dried extract gave the crude product which was recrystallized from diethyl ether, 28.6 g. (76% yield), m.p. 126°–127° C.

The NMR (CDCl₃) spectrum showed absorption at 1.28 (t, J=7 Hz, CH₃), 3.56 (s, CH₂), 3.79 (q, J=7 Hz, NCH₂), 6.89 (d, J=8.5 Hz, ArH), 7.7 (bs, ArH), 7.74 (bd, ArH) and 9.98 (s, CHO) ppm.

A2. 1-ethyl-5(trans-carbomethoxyvinylene)oxindole

To a slurry of 1.74 g. (72.7 mmoles) of sodium hydride in 100 ml. of tetrahydrofuran and 50 ml. of dimethylformamide at 0° C. was added slowly 13.2 g. (72.7 mmoles) of methyl dimethylphosphonoacetate. To the resulting clear solution was added over a 10 minute period 10 g. (52.9 mmoles) of 1-ethyl-5-formyloxindole in 50 ml. of tetrahydrofuran and 50 ml. of dimethylformamide. The reaction was stirred for 10 minutes and was then added to 1 l. of ice and water and 400 ml. of diethyl ether. The organic layer was separated and washed with water (1×300 ml.) and a saturated brine solution (1×300 ml.). The aqueous layer was further extracted diethyl ether. The extracts were combined, dried and concentrated to give the crude product. Recrystallization from ether gave 12.9 g. (100% yield) of the titled intermediate.

The NMR (CDCl₃) spectrum showed absorption at 1.28 (t, J=7 Hz, CH₃), 3.53 (s, CH₂), 3.79 (q, J=7 Hz, NCH₂), 3.8 (s, OCH₃), 6.35 (d, J=15 Hz, vinyl H), 6.8 (d, J=8 Hz, ArH), 7.4 (m, ArH) and 7.61 (d, J=15 Hz, vinyl H) ppm.

A3. 1-ethyl-5-(2-carbomethoxyethyl)oxindole

A mixture of 12.9 g. (52.6 mmoles) of 1-ethyl-5-(trans-carbomethoxyvinylene)oxindole and 2.0 g. 5% palladium-on-carbon (50% water) in 400 ml. of methanol was shaken in a hydrogen atmosphere at an initial pressure of 1 atm. After 1 hour the catalyst was filtered and the filtrate evaporated. The residue was dissolved in methylene chloride, dried over magensium sulfate and the solvent evaporated to give 12.9 g. (99% yield) of the desired product.

The NMR (CDCl₃) spectrum showed absorption at 1.24 (t, J=7 Hz, CH₃), 2.4-3.2 (m, CH₂), 3.45 (s, CH₂), 3.65 (s, OCH₃), 3.80 (q, J=7 Hz, NCH₂), 6.7 (d, J=8 Hz, ArH) and 7.05 (m, ArH) ppm.

A4. 1-ethyl-5-(2-carboxyethyl)oxindole

To a solution of 12.9 g. (52.2 mmoles) of 1-ethyl-5-(2-carbomethoxyethyl)oxindole in 53 ml. of methanol was added 112.5 ml. of 1N sodium hydroxide solution. After stirring for 1 hour the reaction mixture was acidified by the addition of 165 ml. of 1N hydrochloric acid. The precipitated product was filtered and dried, 11.39 g. (93% yield).

The NMR (CDCl₃) spectrum showed absorption at 1.27 (t, J=7 Hz, CH₃), 2.2-3.1 (m, CH₂), 3.48 (s, CH₂), 3.79 (q, J=7 Hz, NCH₂), 6.67 (d, J=8 Hz, ArH) and 7.1 (m, ArH) ppm.

A5. 1-ethyl-2,7-dioxo-2,3,5,6-tetrahydro-7H-cyclopenta[f]indole

To a solution of 6.99 g. (30 mmoles) of 1-ethyl-5-(2-carboxyethyl)oxindole in 120 ml. of methylene chloride at 25° C. was added 6.86 g. (33 mmoles) of phosphorous pentachloride. After stirring 25 minutes the reaction was cooled to −15° C. and 16 g. (0.12 mole) of aluminum chloride was added. The mixture was stirred at −15° C. for 1.5 hours and 2.5 hours at 0° C. The mixture was then treated with 200 ml. of ice water and 200 ml. of methylene chloride. The organic phase was separated and the aqueous again extracted with the same solvent (100 ml.). The combined extracts were washed with a saturated sodium bicarbonate solution (1×200 ml.) and dried over sodium sulfate. The solvent was removed and the residue recrystallized from diethyl ether to give 5.24 g. (81% yield) of the titled intermediate, m.p. 175° C.

The NMR (CDCl₃) spectrum showed absorption at 1.28 (t, J=7 Hz, CH₃), 2.75 (m, CH₂), 3.15 (m, CH₂), 3.59 (s, CH₂), 3.85 (q, J=7 Hz, NCH₂), 7.12 (s, ArH) and 7.34 (bs, ArH) ppm.

Starting with the appropriate 1-substituted-5-hydroxyoxindole and following the procedure of Preparation A, 1-methyl-2,7-dioxo-2,3,5,6-tetrahydro-7H-cyclopenta[f]indole, 1-phenyl-2,7-dioxo-2,3,5,6-tetrahydro-7H-cyclopenta[f]indole, 1-n-propyl-2,7-dioxo-2,3,5,6-tetrahydro-7H-cyclopenta[f]indole and 1-i-propyl-2,7-dioxo-2,3,5,6-tetrahydro-7H-cyclopenta[f]indole are prepared.

PREPARATION B

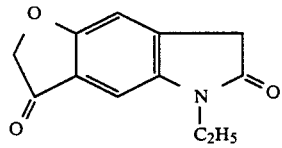

5-Ethyl-3,6-dioxo-2,3,6,7-tetrahydro-furo[2,3-f]indole

B1. 1-ethyl-5-chloroacetoxyoxindole

To a slurry of 100 g. (0.565 mole) of 1-ethyl-5-hydroxyoxindole in 91.3 ml. (1.13 moles) of pyridine and 565 ml. of dichloromethane at 0° C. was added dropwise a solution of 89.3 ml. (1.13 moles) of chloroacetyl chloride in 100 ml. of dichloromethane. The reaction mixture was allowed to stir for 15 minutes, and was then added to 1 l. of ice cold 2N hydrochloric acid and 500 ml. of dichloromethane. The aqueous layer was extracted once again with 300 ml. of dichloromethane and the combined organic extracts washed once with 500 ml. of a saturated brine solution, dried over magnesium sulfate and concentrated to give the desired product in quantitative yield. A small sample was crystallized from hexane, m.p. 53°-57° C.

The NMR spectrum (CDCl₃) showed absorption at 1.23 (J=7 Hz, CH₃), 3.5 (CH₂), 3.72 (J=7 Hz, NCH₂), 4.26 (ClCH₂) and 6.6-7.1 (ArH) ppm.

B2. 5-ethyl-3,6-dioxo-2,3,6,7-tetrahydro-furo[2,3-f]indole

To 142.9 g. (0.565 mole) of 1-ethyl-5-chloroacetoxyoxindole was added slowly 301 g. (2.26 moles) of aluminum chloride, and the resulting reaction mixture heated to 165° C. for one hour and then allowed to stir for 15 minutes. The hot reaction mixture was added to 4 l. of ice and water and the resulting precipitate filtered and dried. The aqueous filtrate was extracted (6×300 ml.) with dichloromethane, and the combined extract dried over magnesium sulfate and concentrated to dryness. The residue was combined with filtered product and recrystallized from ethyl acetate, 85.9 g. (70%), m.p. 181°-184° C.

The NMR spectrum (CDCl₃) showed absorption at 1.29 (J=7 Hz, CH₃), 3.6 (CH₂), 3,78 (J=7 Hz, NCH₂), 4.66 (OCH₂), 6.99 (ArH) and 7.05 (ArH) ppm.

Starting with the requisite 1-substituted-5-hydroxyoxindole and following the procedures of Preparation B, 5-methyl-3,6-dioxo-2,3,6,7-tetrahydro-furo[2,3-f]indole, 5-phenyl-3,6-dioxo-2,3,6,7-tetrahydro-furo[2,3-f]indole, 5-n-propyl-3,6-dioxo-2,3,6,7-tetrahydro-furo[2,3-f]indole and 5-i-propyl-3,6-dioxo-2,3,6,7-tetrahydro-furo[2,3-f]indole are prepared.

PREPARATION C

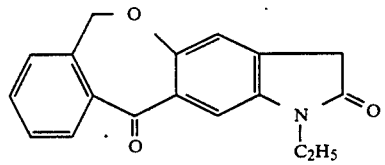

1-Ethyl-2,3,6,11-tetrahydro-2,11-dioxo-[2]-benzoxepino[3,4-f]indole

C1. 1-ethyl-5-(2-carboxybenzyloxy)oxindole

To a solution of 2.24 g. (54.3 mmoles) of sodium hydroxide in 450 ml. of methanol was added 9.63 g. (54.3 mmoles) of 1-ethyl-5-hydroxyoxindole and the resulting solution concentrated in vacuo to dryness at 65° C. The residual sodium salt was mixed with 10.7 g. (79.8 mmoles) of phthalide and the mixture heated one hour at 185° C. An additional 4.0 g. (29.9 mmoles) of phthalide was added and the heating continued at 220° C. for 20 minutes. The reaction was cooled, the solids washed with diethyl ether and the remaining solids partitioned between 1N hydrochloric acid and diethyl ether. The organic phase was separated and extracted with a saturated sodium bicarbonate solution. The bicarbonate solution was separated, acidified with 4N hydrochloric acid and extracted with diethyl ether. The ether layer was separated, dried over magnesium sulfate and concentrated to give a solid. Recrystallization from methanol gave 4.0 g. (24% yield) of the desired product, m.p. 180°–181° C.

Anal. Calcd. for $C_{18}H_{17}O_4N$: C, 69.4; H, 5.5; N, 4.5. Found: C, 69.5; H, 5.5; N, 4.5.

C2. 1-ethyl-2,3,6,11-tetrahydro-2,11-dioxo-[2]benzoxepino[3,4-f]indole

To a suspension of 5.0 g. (16.1 mmoles) of 1-ethyl-5-(2-carboxybenzyloxy)oxindole in 100 ml. of methylene chloride was added 3.34 g. (16.1 mmoles) of phosphorous pentachloride and the reaction mixture allowed to stir 30 minutes at 25° C. The reaction mixture was cooled to −15° C. and 8.56 g. (64.4 mmoles) of aluminum chloride was added. The resulting mixture was allowed to stir at room temperature for 30 minutes and was then added to ice. The organic phase was separated, dried over magnesium sulfate and concentrated to give the desired product which was recrystallized from ethyl acetate-hexane, 2.3 g (69% yield), m.p. 186.5°–188.5° C.

The NMR spectrum (CDCl$_3$) showed absorption at 1.24 (t, J=7 Hz, CH$_3$), 3.45 (s, CH$_2$), 3.8 (q, J=7 Hz, NCH$_2$), 5.11 (s, OCH$_2$) and 6.8–8.0 (m, ArH) ppm.

Starting with the 5-hydroxyoxindole and using the procedure of Preparation C, 1-methyl-2,3,6,11-tetrahydro-2,11-dioxo-[2]benzoxepino[3,4-f]indole, 1-n-propyl-2,3,6,11-tetrahydro-2,11-dioxo[2]benzoxepino[3,4-f]indole and 1-i-propyl-2,3,6,11-tetrahydro-2,11-dioxo-[2]benzoxepino[3,4-f]indole are prepared.

PREPARATION D

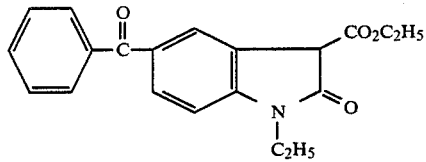

Ethyl 1-ethyl-5-benzoyloxindole-3-carboxylate

D1. 1-ethyl-5-benzoyloxindole

To a mixture of 26.18 g. (186 mmoles) of benzoyl chloride and 32.95 g. of aluminum chloride in 30 ml. of nitrobenzene was gradually added 10.0 g. (62.1 mmoles) of 1-ethyloxindole. The reaction mixture was heated to 100° C. for one hour, cooled and added to 2 l. of ice-water with stirring. The mixture was extracted with methylene chloride (5×200 ml.) and the extracts dried over magnesium sulfate and concentrated in vacuo. The nitrobenzene was distilled from the residue under high vacuum and the residue treated with diethyl ether to induce crystallization. The resulting solids were filtered and recrystallized from methylene chloride petroleum ether, 7.05 g. (42.8% yield), m.p. 134°–136° C.

The NMR (CDCl$_3$) spectrum showed absorption at 1.28 (t, J=7 Hz, CH$_3$), 3.52 (s, CH$_2$), 3.79 (q, J=7 Hz, CH$_2$), 6.8 (d, J=8 Hz, ArH) and 7.6–8.0 (m, ArH) ppm.

In a similar manner were prepared 1-ethyl-5-(4-chlorobenzoyl)oxindole, m.p. 154°–156° C.; 1-ethyl-5-(4-fluorobenzoyl)oxindole, m.p. 110°–120° C.; 1-ethyl-5-(4-methylbenzoyl)oxindole, m.p. 169°–170° C.; 1-ethyl-5-(4-cyanobenzoyl)oxindole, m.p. 163°–168° C.

D2. ethyl 1-ethyl-5-benzoyloxindole-3-carboxylate

To a solution of 1.89 g. of sodium metal in 55 ml. of ethanol cooled to 0° C. was added 9.96 ml. of diethyl carbonate followed by 6.5 g. (27.43 mmoles) of 1-ethyl-5-benzoyloxindole. After heating for 2 hours at 65° C. on an oil bath, the reaction mixture was poured into a cold mixture of 250 ml. 1N hydrochloric, 250 ml. of a saturated brine solution and 200 ml. of methylene chloride. The organic phase was separated, dried and concentrated in vacuo. The excess diethylcarbonate was removed under high vacuum and the residue recrystallized from methylene chloride and cyclohexane, 2.1 g. 1st crop and 3.78 g. 2nd crop.

The NMR spectrum (CDCl$_3$) showed absorption at 1.29 (m, 2CH$_3$), 3.6–4.6 (m, 2CH$_2$) and 6.8–8.3 (m, ArH) ppm.

In a similar manner were prepared methyl 1-ethyl-5-(4-chlorobenzoyl)oxindole-3-carboxylate, m.p. 115°–118° C.; methyl 1-ethyl-5-(4-fluorobenzoyl)oxindole-3-carboxylate, m.p. 90°–100° C. (dec.); and methyl 1-ethyl-5-(4-methylbenzoyl)oxindole-3carboxylate, m.p. 110°–115° C.

PREPARATION E

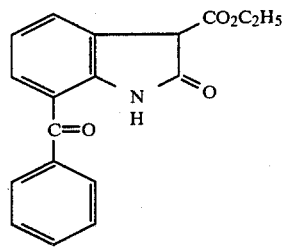

Ethyl 7-benzoyloxindole-3-carboxylate

To a slurry of 365 mg. of sodium hydride in 8 ml. of dimethylformamide at 0° C. was gradually added 1.0 g. (4.22 mmoles) of 7-benzoyloxindole, and the mixture allowed to stir for 10 minutes in an ice bath. Diethyl carbonate (1.53 g., 12.7 mmoles) was added and the reaction mixture allowed to stir at ice bath temperatures for 3 hours. The mixture was then poured into 200 ml. of ice and water and the resulting precipitate filtered, washed with water and vacuum dried, 940 mg. The crude product was slurried in diethyl ether, filtered and the filtrate extracted with 0.1N aqueous sodium hydroxide solution. The base layer was separated and acidified with hydrochloric acid. The resulting precipitate was filtered and dried, 109 mg., m.p. 134° C. (dec.).

The NMR spectrum (CDCl$_3$) showed absorption at 1.42 (t, J=7 Hz, CH$_3$), 4.42 (q, J=7 Hz, CH$_2$), 6.8–8.3 (m, ArH) and 10.4 (bs, NH) ppm.

PREPARATION F

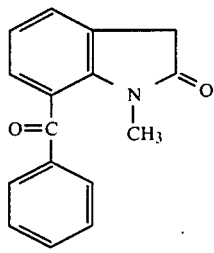

1-Methyl-7-benzoyloxindole

F1. 1-methyl-7-benzoylindole

A mixture of 8.57 g. (38.8 mmoles) of 7-benzoylindole, 5.38 g. (42.7 mmoles) of dimethyl sulfate and 5.12 g. of 85% potassium hydroxide in 40 ml. of acetone was heated to reflux for 75 minutes. The mixture was poured into 500 ml. of water and extracted with methylene chloride. The organic phase was separated, dried and concentrated. The residue was chromatographed on silica gel using methylene chloride-hexane as the eluant. The fractions containing the product were combined and concentrated to dryness, 6.5 g.

The NMR spectrum (CDCl$_3$) showed absorption at 3.6 (s, CH$_3$), 6.52 (d, J=4 Hz, vinyl H), 7.0 (d, J=4 Hz, vinyl H) and 7.1–8.0 (m, ArH) ppm.

F2. 1-methyl-7-benzoyloxindole

To a solution of 6.17 g. (26.25 mmoles) of 1-methyl-7-benzoylindole in 62 ml. of methylene chloride was added 3.58 g. (26.25 mmoles) of 98% N-chlorosuccinimide and the mixture allowed to stir for 90 minutes. An additional 720 mg. of N-chlorosuccinimide was added and stirring continued for 2 hours. The reaction mixture was concentrated in vacuo and 52 ml. of acetic acid added. The mixture was heated to 80° C. and 27 ml. of 85% phosphoric acid was added. The temperature was raised to reflux for 90 minutes and the reaction was cooled and poured into 200 ml. of ice and water. The precipitate was filtered, dissolved in methylene chloride and the solution dried with magnesium sulfate. Removal of the solvent gave a residue which was dissolved in 5% diethyl ether-methylene chloride and filtered through silica gel. The fractions were collected, combined and concentrated to give 4.0 g. of the product as a viscous oil.

The NMR spectrum (CDCl$_3$) showed absorption at 2.99 (s, CH$_3$), 3.55 (s, CH$_2$) and 7.0–8.0 (m, ArH) ppm.

PREPARATION G

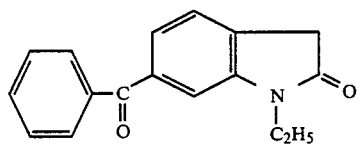

1-Ethyl-6-benzoyloxindole

G1. diethyl 2-nitro-4-benzoylphenylmalonate

To a solution of sodium ethoxide, formed by reacting 4.6 g. (0.2 mole) of sodium metal with 200 ml. of ethanol, at 0° C. was added 32 g. (0.2 mole) of diethyl malonate followed by 26.1 g. (0.1 mole) of 4-chloro-3-nitrobenzophenone. The mixture was allowed to stir at room temperature for 2 hours and was then poured into 400 ml. of ice cold 2N hydrochloric acid and 300 ml. of methylene chloride. The organic layer was separated, dried over magnesium sulfate and concentrated to an oil. The residual oil was induced to crystallize by trituration with hexane containing trace amounts of diisopropyl ether, 34.75 g., m.p. 68°–70° C. The sample was further purified by trituration with hot hexanediisopropyl ether, 30.84 g. (80% yield).

Anal. Calcd. for C$_{20}$H$_{19}$NO$_7$: C, 62.3; H, 5.0; N, 3.6. Found: C, 62.3; H, 4.9; N, 3.6.

G2. 2-nitro-4-benzoylphenylacetic acid

A mixture of 14 g. (36.3 mmoles) of diethyl 2-nitro-4-benzoylphenylmalonate, 300 ml. of 4N hydrochloric acid and 300 ml. of dioxane was heated to reflux for 10 hours. The reaction mixture was concentrated in vacuo and the crude product was triturated with hot methylene chloride, 9.88 g. (95% yield), m.p. 168°–170° C.

Anal. Calcd. for C$_{15}$H$_{11}$NO$_5$: C, 63.2; H, 3.9; N, 4.9. Found: C, 62.9; H, 4.0; N, 4.9.

G3. ethyl 2-nitro-4-benzoylphenylacetate

To a solution of 13.8 g. (48.4 mmoles) of 2-nitro-4-benzoylphenylacetic acid in 150 ml. of 1,2-dimethoxyethane at 15° C. was added 5.87 g. (58.1 mmole) of triethylamine. After 5 minutes 5.75 g. (53.2 mmoles) of ethylchloroformate was added and the reaction mixture allowed to stir at 10° C. for 15 minutes. Ethanol (15 ml.) was added and the reaction subsequently was added to a mixture of diethyl ether and a saturated brine solution. The organic phase was separated, dried over magnesium sulfate and concentrated to an oil, which was induced to crystallize, 5 14.3 g. (94% yield), m.p. 61°–62° C.

Anal. Calcd. for C$_{17}$H$_{15}$NO$_5$: C, 65.2; H, 4.8; N, 4.5. Found: C, 65.0; H, 4.8; N, 4.3.

G4. ethyl 2-amino-4-benzoylphenylacetate

To a solution of 14 g. (44.7 mmoles) of ethyl 2-nitro-4-benzoylphenylacetate in 225 ml. of ethanol was added 15 g. of wet Raney nickel and the mixture heated to reflux for 1.5 hours. The mixture was filtered and the filtrate concentrated to give a residual oil which was induced to crystallize by trituration with diethyl ether, 7.9 g., m.p. 150°–152° C.

The NMR spectrum (CDCl$_3$) showed absorption at 1.24 (t, J=7 Hz, CH$_3$), 3.61 (s, CH$_2$), 4.13 (q, J=7 Hz, CH$_2$) and 7.0–7.9 (m, ArH) ppm.

G5. 6-benzoyloxinole

A mixture of 5.0 g. (17.6 mmoles) of ethyl 2-amino-4-benzoylphenylacetate and 999 mg. of p-toluenesulfonic acid in 300 ml. of toluene was heated to 110° C. for 5 minutes. The reaction was cooled and added to a mixture of methylene chloride and a saturated sodium bicarbonate solution. The organic phase was separated, dried and concentrated to a solid, 3.68 g. (88% yield), m.p. 206°–208° C.

The NMR spectrum (CDCl$_3$+d$_6$-DMSO) showed absorption at 3.52 (s, CH$_2$), 7.1–7.9 (m, ArH) and 10.1 (bs, NH) ppm.

G6. 1-ethyl-6-benzoyloxindole

To a slurry of 1.28 g. (32 mmoles) of potassium hydride in 8 ml. of dimethylformamide at 0° C. was added 1.77 g. (7.47 mmoles) of 6-benzoyloxindole, followed after a few minutes by 1.2 g. (8 mmoles) of diethyl sulfate. After 30 minutes, the reaction was poured into a mixture of methylene chloride and cold 1N hydrochloric acid. The organic phase was separated, dried and concentrated to dryness. The residue was chromatographed on silica gel using methylene chloride-diethyl ether (5:1, v:v) as the eluant. The fractions containing the product were combined and concentrated to dryness, 352 mg. (18% yield), m.p. 120°–121° C.

Anal. Calcd. for $C_{17}H_{15}NO_2$: C, 77.0; H, 5.7; N, 5.3. Found: C, 76.8; H, 5.7; N, 5.2.

Starting with 6-benzoyloxindole and the appropriate dialkyl sulfate and employing the procedure of Preparation G6, 1-methyl-6-benzoyloxindole, 1-n-propyl-6-benzoyloxindole and 1-i-propyl-6-benzoyloxindole are prepared.

PREPARATION H

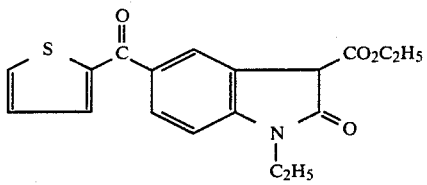

Ethyl 1-ethyl-5-(2-thenoyl)oxindole-3-carboxylate

H1. 1-ethyl-5-(2-thenoyl)oxindole

To a mixture of 27.3 g. (19.9 mmoles) of 2-thenoyl chloride, 30 ml. of nitrobenzene and 32.95 g. of aluminum chloride was gradually added 10 g. (62 mmoles) of 1-ethyloxindole, and the resulting reaction mixture heated at 100° C. for 75 minutes. The reaction was cooled to room temperature and poured into 2 l. of ice and water. The product was extracted with methylene chloride and the dried extract concentrated to dryness, 11.05 g. The product was recrystallized from methylene chloride-hexane, 8.03 g. (47.7% yield)m, m.p. 158°–160° C.

The NMR spectrum (CDCl$_3$) showed absorption at 1.30 (t, J=7 Hz, CH$_3$), 3.59 (s, CH$_2$), 3.81 (q, J=7 Hz, CH$_2$), 6.89 (d, J=8 Hz, ArH), 7.2 (m, ArH) and 7.5–8.0 (m, ArH) ppm.

H2. ethyl 1-ethyl-5-(2-thenoyl)oxindole-3-carboxylate

To sodium ethoxide, formed by adding 2 g. of sodium metal to 58 ml. of ethanol, at 0° C. was added 7.84 g. (28.9 mmoles) of 1-ethyl-5-(2-thenoyl)oxindole followed by 10.24 g. (86.8 mmoles) of diethyl carbonate, and the reaction heated to 65° C. for 2 hours. The reaction mixture was poured into a cold mixture of 250 ml. 1N hydrochloric acid, 250 ml. of a saturated brine solution and 200 ml. of methylene chloride. The organic phase was separated, dried over magnesium sulfate and concentrated in vacuo. The residue was triturated with diethyl ether and filtered. The filtrate was substantially concentrated to dryness under vacuum to give the desired product, 5.4 g. (54.4% yield).

The NMR spectrum (CDCl$_3$) showed absorption at 1.29 (m, 2CH$_3$), 3.5–4.6 (m, 2CH$_2$) and 6.5–8.4 (m, ArH) ppm.

PREPARATION I

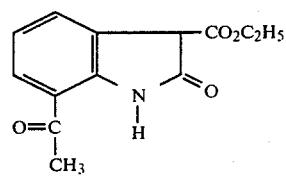

Ethyl 7-acetyoxindole-3-carboxylate

I1. 7-acetyloxindoline

To a solution of 47.35 g. (0.5 mole) of boron tribromide in 300 ml. of toluene at 0° C. was added dropwise a solution of 50 g. (0.42 mole) of indoline and 22.39 g. (0.546 mole) of acetonitrile in 200 ml. of toluene. After stirring for 10 minutes 67.2 g. (0.5 mole) of aluminum chloride was added in portions. The resulting reaction mixture was heated to reflux for 66 hours, cooled to 5° C. and treated with 80 ml. of water and 330 ml. of 2N hydrochloric acid. The resulting mixture was heated to reflux for 2.5 hours, cooled and filtered. The filtrate was set aside and the solids suspended in 500 ml. of water and treated with 2N sodium hydroxide solution until basic. The basic mixture was extracted (2×200 ml.) with methylene chloride and the organic phase separated, dried and concentrated to a solid, 17.2 g. The filtrate which was set aside was made basic with 4N aqueous sodium hydroxide and extracted with methylene chloride. The organic phase was separated, dried and concentrated to a solid, 21.8 g. The combined solids were recrystallized from hexane, 30 g., m.p. 83°–85° C.

The NMR spectrum (CDCl$_3$) showed absorption at 2.53 (s, CH$_3$), 3.05 (bt, J=8 Hz, CH$_2$), 3.75 (bt, J=8 Hz, CH$_2$), 6.5 (dd, J=8 Hz, ArH), 7.13 (bd, J=8 Hz, ArH), 7.15 (b, NH) and 7.4 (bd, J=8 Hz, ArH) ppm.

I2. 7-acetylindole

To 30 g. (0.186 mole) of 7-acetylindoline in 415 ml. of methylene chloride was added 48.5 g. (0.56 mole) of manganese dioxide and the mixture refluxed through a soxhlet filled with 4A molecular sieves for 22 hours. The mixture was cooled and an additional 48.5 g. of manganese dioxide was added. Fresh molecular sieves were added and the refluxing continued for 5 hours. The same amount of manganese dioxide and molecular sieves were added again and the refluxing was continued for one hour. The mixture was filtered and the filtrate concentrated to dryness. The residue was triturated with hexane and filtered, 22.57 g. (76% yield), m.p. 65°–66° C.

The NMR spectrum (CDCl$_3$) showed absorption at 2.69 (s, CH$_3$), 6.52 (dd, J=3 and 3 Hz, vinyl H), 7.12 (d, J=8 Hz, ArH), 7.25 (d, J=3 Hz, vinyl H) and 7.78 (m, ArH) ppm.

I3. 7-acetyloxindole

To a solution of 12.57 g. (79 mmoles) of 7-acetylindole in 187 ml. of methylene chloride was added 11.07 g. (82.9 mmoles) of N-chlorosuccinimide and the reaction allowed to stir at room temperature for 2 hours. The solvent was removed in vacuo and the residue treated with 155 ml. of acetic acid and heated to 80° C. Phosphoric acid (80 ml.) was added and the reaction mixture heated to reflux for 9 hours. The mixture was cooled, the acetic acid removed under vacuum and the residue poured into 500 ml. of ice and water. The product was extracted with methylene chloride, 11.91 g. (65% yield), 174°–175° C.

The NMR spectrum (CDCl$_3$) showed absorption at 2.6 (s, CH$_3$), 3.49 (s, CH$_2$), 7.01 (dd, J=8 and 8 Hz, ArH), 7.25 (d, J=8 Hz, ArH) and 7.66 (d, J=8 Hz, ArH) ppm.

I4. 7-acetyloxindole-3-carboxylate

To a slurry of 1.85 g. of sodium hydride in 49 ml. of dimethylformamide at 0° C. was added 4.5 g. (0.0257 mole) of 7-acetyloxindole. When the evolution of hydrogen ceased 9.1 g. (0.0771 mole) of diethyl carbonate was added and the mixture allowed to stir in the cold for 5 hours. The reaction mixture was poured into 500 ml. of ice and water and 40 ml. of 4N hydrochloric acid. The resulting precipitate was filtered and dried in vacuo, 5.38 g. The product was recrystallized from methylene chloride-diisopropyl ether, 2.27 g. (35.7% yield), m.p. 186°–190° C.

The NMR spectrum (d$_6$-DMSO) showed absorption at 1.32 (t, J=7 Hz, CH$_3$), 2.61 (s, CH$_3$), 4.25 (q, J=7 Hz, CH$_2$), 7.15 (dd, J=7.5 and 7.5 Hz, ArH), 7.6 (d, J=7.5 Hz, ArH), 8.0 (d, J=7.5 Hz, ArH) and 11.1 (bs, 1H) ppm.

In a similar manner, by starting with the appropriate indoline and employing the procedures of Preparation I, the following 7-acetyloxindoles are prepared: ethyl 1-methyl-7-acetyloxindole-3-carboxylate, ethyl 1-ethyl-7-acetyloxindole-3-carboxylate, ethyl 1-n-propyl-7-acetyloxindole-3-carboxylate and ethyl 1-i-propyloxindole-3-carboxylate.

PREPARATION J

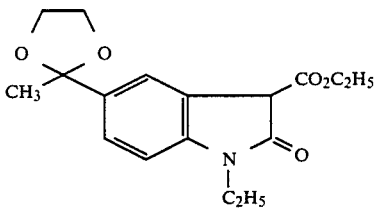

Ethyl 1-ethyl-5-(2-methyl-4,5-dihydro-1,3-dioxol-2-yl)oxindole-3-carboxylate

J1. 1-ethyl-5-acetyloxindole

To a mixture of 29.25 g. (0.373 mole) of acetyl chloride and 65.9 g. of aluminum chloride in 60 ml. of nitrobenzene was added gradually 20.0 (0.124 mole) of 1-ethyloxindole. The reaction warmed to about 45° C. with an evolution of gas. After stirring for one hour the reaction was heated to 100° C. for one hour and allowed to stir at room temperature over night. The reaction mixture was poured into 2 l. of ice with stirring. After 30 minutes the product was filtered, air dried and dissolved in 200 ml. of methylene chloride. The solution was dried over magnesium sulfate and concentrated to dryness. The residue was recrystallized from toluene, 14.44 g. (57.3% yield), m.p. 141°–45° C.

The NMR spectrum (CDCl$_3$) showed absorption at 1.29 (t, J=7 Hz, CH$_3$), 2.56 (s, CH$_3$), 3.52 (s, CH$_2$), 3.82 (q, J=7 Hz, CH$_2$), 6.85 (d, J=8 Hz, ArH) and 7.9 (m, ArH) ppm.

J2. 1-ethyl-5-(2-methyl-4,5-dihydro-1,3-dioxol-2-yl)oxindole

A mixture of 10.0 g. (49.26 mmoles) of 1-ethyl-5-acetyloxindole, 27.4 ml. of ethylene glycol and a trace of p-toluene sulfonic acid in 300 ml. of benzene was refluxed through a soxhlet filled with 4A sieves for 13 hours. The reaction was cooled to room temperature and poured into a saturated sodium bicarbonate solution. The organic layer was separated, dried over magnesium sulfate and concentrated to dryness. The residue was recrystallized from hexane-methylene chloride, 10.79 g. (90% yield), m.p. 95–98%.

The NMR spectrum (CDCl$_3$) showed absorption at 1.22 (t, J=7 Hz, CH$_3$), 1.65 (s, CH$_3$), 3.48 (s, CH$_2$), 3.6–4.2 (m, (CH$_2$O)$_2$), 6.73 (d, J=8 Hz, ArH) and 7.35 (m, ArH) ppm.

J3. ethyl 1-ethyl-5-(2-methyl-4,5-dihydro-1,3-dioxol-2-yl)oxindole-3-carboxylate Sodium (1.39 g.) was reacted with 40 ml. of ethanol and cooled to 0° C. in an ice bath. To the cold solution was added 7.3 ml. (60.7 mmoles) of diethyl carbonate followed by 5.0 g. (20.24 mmoles) of 1-acetyl-5-(2-methyl-4,5-dihydro-1,3-dioxol-2-yl)oxindole and the resulting reaction mixture heated to 65° C. for 2 hours. The reaction was cooled to room temperature and added to a mixture of ice 200 ml. water and 200 ml. methylene chloride containing 3.45 ml. of acetic acid. The organic phase was separated, washed with a saturated sodium bicarbonate solution and dried over magnesium sulfate. Removal of the solvent gave 4.99 g. (70% yield) of product m.p. 73°–75° C.

The NMR spectrum (CDCl$_3$) showed absorption at 1.28 (t, J=7 Hz, CH$_3$), 1.65 (s, CH$_3$), 3.5–4.6 (m, 4CH$_2$, CH), 6.8 (d, J=8 Hz, ArH) and 7.1–7.6 ArH) ppm.

By starting with the requisite oxindole and employing the procedure of Preparation J, the following intermediates are prepared:

ethyl 5-(2-methyl-4,5-dihydro-1,3-dioxol-2-yl)-oxindole-3-carboxylate, ethyl 1-methyl-5-(2-methyl-4,5-dihydro-1,3-dioxol-2-yl)oxindole-3-carboxylate, ethyl 1-n-propyl-5-(2-methyl-4,5-dihydro-1,3-dioxol-2-yl)oxindole-3-carboxylate and ethyl 1-i-propyl-5-(2-methyl-4,5-dihydro-1,3-dioxol-2-yl)oxindole-3-carboxylate.

Similarly, were prepared ethyl 5-(2-n-pentyl-4,5-dihydro-1,3-dioxol-2-yl-oxindole-3-carboxylate, ethyl 5-(2-isopropyl-4,5-dihydro-1,3-dioxol-2-yl)oxindole-3-carboxylate, ethyl 5-(2-neopentyl-4,5-dihydro-1,3-dioxol-2-yl)oxindole-3-carboxylate and ethyl 5-(2-benzyl-4,5-dihydro-1,3-dioxol-2-yl)oxindole-3-carboxylate.

PREPARATION K

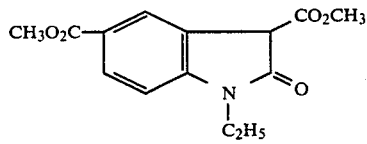

Methyl 1-ethyl-5-methoxycarbonyloxindole-3-carboxylate

K1. 1-ethyl-5-methoxycarbonyloxindole

To 4.0 g. (19.5 mmoles) of 1-ethyl-5-carboxyoxindole (Chem. Ber. 44, 202 (1911) in 120 ml. of dry methanol was bubbled hydrogen chloride gas for about 2 minutes. The resulting solution was heated to reflux for 20 hours and cooled. Evaporation of the methanol to a small volume gave 2.5 g. of desired product, m.p. 97°–98° C.

In a similar manner was prepared 1-ethyl-5-ethoxycarbonyloxindole, m.p. 100°–103° C.

K2. methyl 1-ethyl-5-methoxycarbonyloxindole-3-carboxylate

A mixture of 2.5 g. (11.4 mmoles) of 1-ethyl-5-methoxycarbonyloxindole and 4.14 ml. (49.1 mmoles) of diethyl carbonate in 25 ml. of methanol containing sodium methoxide prepared in situ from 790 mg. (34.2 mmoles) of sodium metal was refluxed for 2.5 hours. The cooled reaction mixture was added to 200 ml. of water and extracted with diethylether (2×100 ml.). The aqueous layer was acidified with 10 ml. of 6N hydrochloric acid and extracted with ethylacetate (2×100 ml.). The organic phase was dried and evaporated to give 4.0 g. of the product as a low melting solid.

In a similar manner, methyl 1-ethyl-5-ethoxycarbonyloxindole-3-carboxylate was prepared as an oil.

PREPARATION L

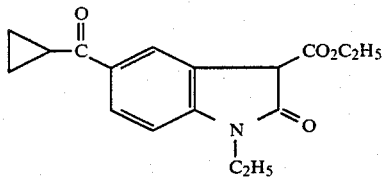

Ethyl 1-ethyl-5-cyclopropylcarbonyloxindole-3-carboxylate

L1. 1-ethyl-5-cyclopropylcarbonyloxindole

In a manner similar to Preparation J1., 10 g. (62 mmoles) of 1-ethyloxindole, 7.2 ml. (78.8 mmoles) of cyclopropylcarbonyl chloride and 51 g. (380 mmoles) of aluminum chloride in 200 ml. of carbon disulfide gave 3.75 of the desired product.

By a similar procedure, 1-ethyl-5-cyclopentyloxindole was prepared as a yellow solid.

L2. ethyl 1-ethyl-5-cyclopropylcarbonyloxindole-3-carboxylate

A mixture of 3.0 g. (13.1 mmoles) of 1-ethyl-5-cyclopropylcarbonyloxindole, 4.75 ml. (39.3 mmoles) of diethyl carbonate and sodium ethoxide generated in situ from 900 mg. (39.3 mmoles) of sodium metal in 75 ml. of ethanol was warmed to 65° C. for 3 hours. The reaction mixture was cooled, concentrated in volume and partitioned between water and methylene chloride. The pH of the mixture was adjusted to 1 and the organic layer separated. The aqueous layer was further extracted with methylene chloride. The extracts were combined, washed with a brine solution, dried and concentrated to give 3.5 g. of product as a red oil.

In a similar manner ethyl 1-ethyl-5-cyclopentylcarbonyloxindole-3-carboxylate was prepared.

I claim:

1. Compounds of the formula

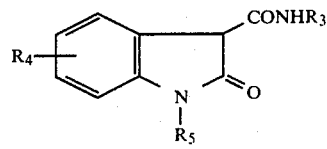

and the pharaceutically acceptable base salts thereof, wherein $R_5$ is selected from the group consisting of hydrogen and alkyl containing one to three carbon atoms; $R_3$ is selected from the group consisting of phenyl, fluorophenyl, trifluoromethylphenyl, methoxyphenyl, chlorophenyl, difluorophenyl, pyridyl, 2-thiazolyl, 5-methyl-2-thiazolyl, 5-methyl-3-isoxazolyl, 2-thiadiazolyl and 2-pyrimidyl; and $R_4$ is a substituent at the 5, 6 or 7-position of the oxindole selected from the group consisting of alkanoyl having two to six carbon atoms, cycloalkanoyl having four to six carbon atoms, 2-thenoyl, benzoyl, phenylacetyl and substituted benzoyl wherein said substituent is selected from the group consisting of fluoro, chloro, methyl and cyano.

2. A compound of claim 1, wherein $R_5$ is alkyl containing one to three carbon atoms and $R_4$ is benzoyl.

3. The compound of claim 2, wherein $R_5$ is methyl; $R_3$ is 4-fluorophenyl and $R_4$ is benzoyl at the 5-position of the oxindole.

4. The compound of claim 2, wherein $R_5$ is ethyl, $R_3$ is 4-fluorophenyl and $R_4$ is benzoyl at the 5-position of the oxindole.

5. The compound of claim 2, wherein $R_5$ is ethyl, $R_3$ is 5-methyl-2-thiazolyl and $R_4$ is benzoyl at the 5-position of the oxindole.

6. A compound of claim 1 wherein $R_5$ is hydrogen and $R_4$ is benzoyl.

7. The compound of claim 6, wherein $R_3$ is phenyl and $R_4$ is benzoyl at the 5-position of the oxindole.

8. The compound of claim 6, wherein $R_3$ is 2,4-difluorophenyl and $R_4$ is benzoyl at the 5-position of the oxindole.

9. A compound of claim 1, wherein $R_5$ is alkyl containing from one to three carbon atoms and $R_4$ is 2-thenoyl.

10. The compound of claim 9, wherein $R_5$ is ethyl, R is 4-fluorophenyl and $R_4$ is 2-thenoyl at the 5-position of the oxindole.

11. The compound of claim 9, wherein $R_5$ is ethyl, $R_3$ is 2,4-difluorophenyl and $R_4$ is 2-thenoyl at the 5-position of the oxindole.

12. A compound of claim 1, wherein $R_5$ is alkyl containing from one to three carbon atoms and $R_4$ is acetyl.

13. The compound of claim 12, wherein $R_5$ is ethyl, $R_4$ is acetyl at the 5-position of the oxindole and $R_3$ is 2,4-difluorophenyl.

14. A method of treating an inflammatory disease in a mammalian subject, which comprises administering to said subject an inflammatory disease treating amount of a compound according to claim 1.

15. A pharmaceutical composition, which comprises a pharmaceutically-acceptable carrier and an inflammatory disease treating amount of a compound according to claim 1, and wherein the weight-ratio of the pharmaceutically-acceptable carrier to said compound is in the range of from 1:4 to 20:1.

* * * * *